US008785871B2

(12) United States Patent
Muraoka

(10) Patent No.: US 8,785,871 B2
(45) Date of Patent: Jul. 22, 2014

(54) RADIOGRAPHIC-IMAGE CAPTURING DEVICE AND RADIOGRAPHIC-IMAGE CAPTURING SYSTEM

(75) Inventor: Taketoh Muraoka, Hino (JP)

(73) Assignee: Konica Minolta Medical & Graphic, Inc. (JP)

( * ) Notice: Subject to any disclaimer, the term of this patent is extended or adjusted under 35 U.S.C. 154(b) by 209 days.

(21) Appl. No.: 13/384,263

(22) PCT Filed: Feb. 10, 2010

(86) PCT No.: PCT/JP2010/051943
§ 371 (c)(1),
(2), (4) Date: Jan. 16, 2012

(87) PCT Pub. No.: WO2011/010480
PCT Pub. Date: Jan. 27, 2011

(65) Prior Publication Data
US 2012/0119100 A1    May 17, 2012

(30) Foreign Application Priority Data

Jul. 24, 2009   (JP) ................................ 2009-172634

(51) Int. Cl.
*H01L 27/146*   (2006.01)
*H04N 5/32*   (2006.01)
(52) U.S. Cl.
CPC ..................................... *H04N 5/32* (2013.01)
USPC .................................................. 250/370.09
(58) Field of Classification Search
CPC ................... H04N 5/32; A61B 6/4233; G06T 2207/10116
USPC .......................... 250/370.01–370.15; 378/98.8
See application file for complete search history.

(56) References Cited

U.S. PATENT DOCUMENTS 5,272,535 A * 12/1993 Elabd ............................ 348/314
2011/0079727 A1 * 4/2011 Prescher et al. ............ 250/370.1

FOREIGN PATENT DOCUMENTS

| JP | 6-342099 A | 12/1994 |
| JP | 09-073144 A | 3/1997 |
| JP | 2000-275350 A | 10/2000 |
| JP | 2003-234967 A | 8/2003 |
| JP | 2005-287927 A | 10/2005 |
| JP | 2006-058124 A | 3/2006 |
| JP | 2006-263322 A | 10/2006 |

OTHER PUBLICATIONS

International Search Report for International Application No. PCT/JP2010/051943 mailing date of Mar. 23, 2010 with English translation.

\* cited by examiner

*Primary Examiner* — Kiho Kim
(74) *Attorney, Agent, or Firm* — Cantor Colburn LLP

(57) ABSTRACT

The radiographic-image capturing device is provided with: a detecting unit that has multiple scanning lines and multiple signal lines arranged so as to intersect with each other, and has multiple radiation detection elements arranged two-dimensionally at each of the areas partitioned by the multiple scanning lines and multiple signal lines; a reading circuit that reads electric charges from the radiation detection elements via the signal lines, and converts the electric charges to electric signals, and outputs the electric signals as image data, for each of the radiation detection elements; and compressing means for compressing image data of each of the radiation detection elements. The compressing means creates difference data between the image data of adjacent radiation detection elements, for each of the image data outputted from multiple radiation detection elements connected to the same signal line, and compresses this difference data.

16 Claims, 21 Drawing Sheets

FIG. 19A

| | | | | | |
|---|---|---|---|---|---|
| L1 | D(1, 1) | D(1, 2) | D(1, 3) | D(1, 4) | D(1, 5) |
| L2 | D(2, 1) | D(2, 2) | D(2, 3) | D(2, 4) | D(2, 5) |
| L3 | D(3, 1) | D(3, 2) | D(3, 3) | D(3, 4) | D(3, 5) |
| L4 | D(4, 1) | D(4, 2) | D(4, 3) | D(4, 4) | D(4, 5) |
| L5 | D(5, 1) | D(5, 2) | D(5, 3) | D(5, 4) | D(5, 5) |
| L6 | D(6, 1) | D(6, 2) | D(6, 3) | D(6, 4) | D(6, 5) |
| L7 | D(7, 1) | D(7, 2) | D(7, 3) | D(7, 4) | D(7, 5) |
| L8 | D(8, 1) | D(8, 2) | D(8, 3) | D(8, 4) | D(8, 5) |
| L9 | D(9, 1) | D(9, 2) | D(9, 3) | D(9, 4) | D(9, 5) |
| L10 | D(10, 1) | D(10, 2) | D(10, 3) | D(10, 4) | D(10, 5) |
| L11 | D(11, 1) | D(11, 2) | D(11, 3) | D(11, 4) | D(11, 5) |
| L12 | D(12, 1) | D(12, 2) | D(12, 3) | D(12, 4) | D(12, 5) |

FIG. 19B

| | | | | | |
|---|---|---|---|---|---|
| L1 | D(1, 1) | D(1, 2) | D(1, 3) | D(1, 4) | D(1, 5) |
| L4 | D(4, 1) | D(4, 2) | D(4, 3) | D(4, 4) | D(4, 5) |
| L7 | D(7, 1) | D(7, 2) | D(7, 3) | D(7, 4) | D(7, 5) |
| L10 | D(10, 1) | D(10, 2) | D(10, 3) | D(10, 4) | D(10, 5) |

FIG. 20

| L2 | D(2, 1) | D(2, 2) | D(2, 3) | D(2, 4) | D(2, 5) |
|---|---|---|---|---|---|
| L3 | D(3, 1) | D(3, 2) | D(3, 3) | D(3, 4) | D(3, 5) |
| L5 | D(5, 1) | D(5, 2) | D(5, 3) | D(5, 4) | D(5, 5) |
| L6 | D(6, 1) | D(6, 2) | D(6, 3) | D(6, 4) | D(6, 5) |
| L8 | D(8, 1) | D(8, 2) | D(8, 3) | D(8, 4) | D(8, 5) |
| L9 | D(9, 1) | D(9, 2) | D(9, 3) | D(9, 4) | D(9, 5) |
| L11 | D(11, 1) | D(11, 2) | D(11, 3) | D(11, 4) | D(11, 5) |
| L12 | D(12, 1) | D(12, 2) | D(12, 3) | D(12, 4) | D(12, 5) |

FIG. 21

| | | | | | | |
|---|---|---|---|---|---|---|
| L1 | D(1, 1) | D(1, 2) | D(1, 3) | D(1, 4) | D(1, 5) | |
| L2 | D(2, 1) | D(2, 2) | D(2, 3) | D(2, 4) | D(2, 5) | |
| L3 | D(3, 1) | D(3, 2) | D(3, 3) | D(3, 4) | D(3, 5) | |
| L4 | D(4, 1) | D(4, 2) | D(4, 3) | D(4, 4) | D(4, 5) | |
| L5 | D(5, 1) | D(5, 2) | D(5, 3) | D(5, 4) | D(5, 5) | |
| L6 | D(6, 1) | D(6, 2) | D(6, 3) | D(6, 4) | D(6, 5) | |
| L7 | D(7, 1) | D(7, 2) | D(7, 3) | D(7, 4) | D(7, 5) | |
| L8 | D(8, 1) | D(8, 2) | D(8, 3) | D(8, 4) | D(8, 5) | |
| L9 | D(9, 1) | D(9, 2) | D(9, 3) | D(9, 4) | D(9, 5) | |
| L10 | D(10, 1) | D(10, 2) | D(10, 3) | D(10, 4) | D(10, 5) | |
| L11 | D(11, 1) | D(11, 2) | D(11, 3) | D(11, 4) | D(11, 5) | |
| L12 | D(12, 1) | D(12, 2) | D(12, 3) | D(12, 4) | D(12, 5) | |

FIG. 22

|     | 1 | 2 | 3 | 4 | 5 |
|-----|---|---|---|---|---|
| L1  | D(1, 1)  | D(1, 2)  | D(1, 3)  | D(1, 4)  | D(1, 5)  |
| L2  | D(2, 1)  | D(2, 2)  | D(2, 3)  | D(2, 4)  | D(2, 5)  |
| L3  | D(3, 1)  | D(3, 2)  | D(3, 3)  | D(3, 4)  | D(3, 5)  |
| L4  | D(4, 1)  | D(4, 2)  | D(4, 3)  | D(4, 4)  | D(4, 5)  |
| L5  | D(5, 1)  | D(5, 2)  | D(5, 3)  | D(5, 4)  | D(5, 5)  |
| L6  | D(6, 1)  | D(6, 2)  | D(6, 3)  | D(6, 4)  | D(6, 5)  |
| L7  | D(7, 1)  | D(7, 2)  | D(7, 3)  | D(7, 4)  | D(7, 5)  |
| L8  | D(8, 1)  | D(8, 2)  | D(8, 3)  | D(8, 4)  | D(8, 5)  |
| L9  | D(9, 1)  | D(9, 2)  | D(9, 3)  | D(9, 4)  | D(9, 5)  |
| L10 | D(10, 1) | D(10, 2) | D(10, 3) | D(10, 4) | D(10, 5) |
| L11 | D(11, 1) | D(11, 2) | D(11, 3) | D(11, 4) | D(11, 5) |
| L12 | D(12, 1) | D(12, 2) | D(12, 3) | D(12, 4) | D(12, 5) |

RADIOGRAPHIC-IMAGE CAPTURING DEVICE AND RADIOGRAPHIC-IMAGE CAPTURING SYSTEM

CROSS REFERENCE TO RELATED APPLICATIONS

This is a U.S. national stage of application No. PCT/JP2010/051943, filed on Feb. 10, 2010. Priority under 35 U.S.C. §119(a) and 35 U.S.C. §365(b) is claimed from Japanese Application No. 2009-172634, filed Jul. 24, 2009, the disclosure of which is also incorporated herein by reference.

TECHNICAL FIELD

The present invention relates to a radiographic-image capturing device and a radiographic-image capturing system, and, in particular, to the radiographic-image capturing device which compresses image data and transfers thereof, and the radiographic-image capturing system which receives the above transferred image data to restore them to the original image data.

BACKGROUND TECHNOLOGY

There have been developed various radiographic-image capturing devices such as a so-called direct-type radiographic-image capturing device which generates charges at a detection element according to the irradiated amount of radiation such as x-rays to convert them into electrical signals, and a so-called indirect-type radiographic-image capturing device which converts irradiated radiation into electromagnetic waves having other wavelength such as a visible light with a scintillator or the like, after which, according to the amount of energy of the converted and irradiated electromagnetic waves, generates charges at a photoelectric conversion element such as a photodiode, and converts them into electric signals. In the present invention, the detection element incorporated in the direct-type radiographic-image capturing device, and the photoelectric conversion element incorporated in the indirect-type radiographic-image capturing device, are collectively referred to as a radiation detection element.

The radiographic-image capturing device of this type has been known as an FPD (flat panel detector), and heretofore has been integrally formed with a supporting table (or a Bucky device) (refer, for example, to Patent Document 1), but, in recent years, a portable radiographic-image capturing device, in which the radiation detection element and the like are stored in a housing, was developed and has been practically used (refer, for example, to Patent Documents 2 and 3).

In such a radiographic-image capturing device, a plurality of radiation detection elements are arranged two-dimensionally (in a matrix state) to form a detecting unit, and, in that case, the number of radiation detection elements (that is, the number of pixels) usually amount to several millions to several tens millions or more pixels. For that reason, if image data which were read out from each radiation detection element are transferred to an external device without compression, the transfer time becomes longer. Further, in a portable radiographic-image capturing device incorporating a battery, if the transfer time of image data becomes longer, electric power consumed during the transfer becomes larger, resulting in exhaustion of the battery.

Then, as it is described in, for example, Patent Documents 4 and 5, the read out image data are usually compressed by a data compression method such as reversible compression (also referred to as lossless compression) and irreversible compression (also referred to as lossy compression), to be transferred to an external device such as a console and a server.

It is assumed that, in the case where, for example, the radiographic-image capturing device, in which an image of a part of the body of the patient as a subject, such as the head, the chest, and hands and feet, is captured, and the obtained radiographic image is used for diagnosis or the like as a medical image, is used as a medical image capturing device, as an image data compression method, in general, it is preferable to adopt the reversible compression method in which compression is carried out so that image data before compressed perfectly agree with restored image data rather than the irreversible compression method in which a part of information of image data is lost by compression.

PRIOR ARTS

Patent Documents

Patent Document 1: Japanese Patent Application Publication No. H9-73144
Patent Document 2: Japanese Patent Application Publication No. 2006-58124
Patent Document 3: Japanese Patent Application Publication No. H6-342099
Patent Document 4: Japanese Patent Application Publication No. 2000-275350
Patent Document 5: Japanese Patent Application Publication No. 2005-287927

SUMMARY OF THE INVENTION

Problem to be Solved by the Invention

According to studies conducted by the inventors of the present patent application on an image data compression method which was read out from each radiation detection element after a radiographic-image was captured, it was found that, in the case where conventional reversible compression of image data using, for example, Huffman encoding is carried out, a comparatively large difference in compression ratio Rc of the image data is generated depending on, as they are shown in "a" to "c" of FIG. 23, image capturing locations (the chest, the skull, the lumbar spine, or the like) or the image capturing direction thereof (the front, the side, or the like).

The term "with narrowing down", as it is shown in "d" of FIG. 23, indicates compression ratio Rc of the case of image capturing with narrowing down irradiated area of radiation, in image capturing of the "side of lumbar spine" given in "c" of FIG. 23, to eliminate or reduce radiated portion of radiation which is a surrounding portion of the lumbar spine of the patient and in which the radiographic-image capturing device is directly irradiated (a so-called an area with no image). In this way, the finding that compression ratio Rc increases when irradiated area is narrowed down was also obtained.

Further, "e" and "f" of FIG. 23 indicate compression ratio Rc of the case where radiation was uniformly irradiated on the device without a subject, and "e" indicates a case where the irradiated amount of radiation was small, and "f" indicates a case where the irradiated amount of radiation was increased. It was found that there is such a case that the larger the irradiated amount of radiation on the radiographic-image capturing device, the more decreased the compression ratio Rc of the obtained image data.

In FIG. 23, compression ratio Rc is a value calculated by dividing a value of the amount of data before compression subtracted by the amount of data after compression with the amount of data before compression. Therefore, the higher the compression ratio Rc, the less the amount of data after compression. In the calculation of compression ratios Rc of "a" to "f" of FIG. 23, the same Huffman coding table is used.

As a result of detailed analysis of the cause in which difference in compression ratio Rc in various image capturing conditions as described above is generated, the inventors of the present patent application found a reversible data compression method which further increases image data compression ratio Rc obtained by the radiographic-image capturing device.

The present invention has been achieved in consideration of the above points, and it is an object of the invention to provide a radiographic-image capturing device and a radiographic-image capturing system which is capable of increasing a compression ratio when compressing the image data obtained at radiation-image capturing.

Measures to Solve the Issues

In order to solve the above problems, the radiographic-image capturing device of the present invention is provided with: a detecting unit being provided with a plurality of scanning lines and a plurality of signal lines arranged so as to intersect with each other, and with a plurality of radiation detection elements arranged two-dimensionally at each of the areas partitioned by the above plurality of scanning lines and plurality of signal lines; a read-out circuit for reading out electric charges from the above radiation detection element via the above signal line, and converts the above electric charges to electric signals, and outputs the electric signals as image data, for every above radiation detection element; and a compression means for compressing image data of each of the above radiation detection elements, wherein the above compression means performs compression processing to each of the above image data which was output from the above plurality of radiation detection elements connected with the above same signal lines for every above signal line.

Further, the radiographic-image capturing device of the present invention is provided with: a detecting unit being provided with a plurality of scanning lines and a plurality of signal lines arranged so as to intersect with each other, and with a plurality of radiation detection elements arranged two-dimensionally at each of the areas partitioned by the above plurality of scanning lines and plurality of signal lines; a read-out circuit for reading out electric charges from the above radiation detection elements via the above signal lines, and converts the above electric charges to electric signals, and outputs the electric signals as image data, for every above radiation detection element; and a compression means for compressing image data of each of the above radiation detection elements, wherein the above compression means calculates difference between the above image data of the above radiation detection elements adjoining to each other, to prepare difference data for each of the above image data output from the above plurality of radiation detection elements connected to the above same signal line, and performs compression processing to the aforesaid difference data.

Still further, the radiographic-image capturing device of the present invention is provided with: a detecting unit being provided with a plurality of scanning lines and a plurality of signal lines arranged so as to intersect with each other, and has a plurality of radiation detection elements arranged two-dimensionally at each of the areas partitioned by the above plurality of scanning lines and plurality of signal lines; a read-out circuit for reading out electric charges from the above radiation detection elements via the above signal lines, and converts the above electric charges to electric signals, and outputs the electric signals as image data, for every above radiation detection elements; a thinned-out data preparing means for preparing thinned-out data by thinning-out and abstracting image data from the above image data per scanning line unit; and a compression means for carrying out compression processing to the above thinned-out data, wherein the above compression means performs compression processing to the above thinned-out data adjoining to each other in the signal line direction, or calculates difference for the above thinned-out data adjoining to each other in the signal line direction to prepare difference data, and then performs compression processing to the aforesaid difference data.

Further, the radiographic-image capturing system of the present invention wherein the system is provided with: a radiographic-image capturing device being provided with a transfer means transferring the above image data which was subjected to the above compression processing; and a console for decompressing the above image data transferred from the above radiographic-image capturing device and having been subjected to the above compression processing, into the above original image data to restore them.

Still further, the radiographic-image capturing system of the present invention wherein the system is provided with: a radiographic-image capturing device being provided with a transfer means transferring the above difference data which was subjected to the above compression processing; and a console for decompressing the above image data transferred from the above radiographic-image capturing device and having been subjected to the above compression processing, into the above original difference data, and then, based on the decompressed above original difference data, restoring the above original image data.

Effects of the Invention

According to the radiographic-image capturing device and the radiographic-image capturing system of such the method of the present invention, such a constitution was made that compression processing was carried out for each of image data and each of difference data, which were not in the scanning line direction like in the conventional method, but in the signal line direction perpendicular to the scanning line, that is, each of image data and each of difference data between the image data outputted from a plurality of radiation detection elements connected to the same signal line, therefore, compression processing is carried out for each of image data and each of difference data between the image data read out from the identical read out circuit.

Consequently, it becomes possible to prevent lowering the compression rate due to broadening of image data and difference data depending on variation of output characteristic of each readout circuit as in the conventional compression processing to each of image data and difference data between the image data which form in line in the scanning line direction, whereby it becomes possible to certainly increase the compression ratio when compressing the image data and difference data between the image data obtained at radiographic-image capturing.

In addition, since each of image data and each of difference data between the image data read out from the identical read out circuit are distributed in a normal distribution curve, there is maintained a state that short codes are allotted to data having a high appearance frequency in the compressed image data and the difference data, even if the amount of radiation irradiated on radiographic-image capturing device becomes large. Therefore, it becomes possible to maintain a high compression ratio disregarding the amount of irradiated radiation. Further, due to the reason, it becomes possible to compress the image data and the difference data with a high compression ratio, even in imaging situations where an image of an area with no image is captured in an image.

Furthermore, since the amount of data to be transferred is decreased and transfer time is shortened, because the image data and the difference data may be compressed with a high compression ratio, it becomes possible to lower the total power consumption of the radiographic-image capturing device and the radiographic-image capturing system.

BRIEF DESCRIPTION OF THE DRAWINGS

FIG. 19A is a figure showing an example of each of image data which will be extracted to prepare thinned-out data, and FIG. 19B is a figure showing a state in which extracted thinned-out data are accumulated.

FIG. 20 is a figure showing a state in which remaining data are extracted and accumulated.

FIG. 21 is a figure describing a method for preparing the difference data for the remaining image data based on the thinned-out data.

FIG. 22 is a figure showing another example of each of image data which will be extracted to prepare thinned-out data.

MODE FOR CARRYING OUT THE INVENTION

Hereinafter, embodiments of the radiographic-image capturing device and the radiographic-image capturing system relating to the present invention will be described with reference to figures.

In the following description, a case, in which the radiographic-image capturing device is a so-called indirect-type radiographic-image capturing device which is provided with a scintillator and the like and obtains electric signals by converting irradiated radiation into electromagnetic waves having other wavelength such as a visible light, will be described, but the present invention can be applied to the direct-type radiographic-image capturing device. In addition, a case, in which the radiographic-image capturing device is a portable type, will be described, but the radiographic-image capturing device is also applied to one which is integrally formed with a supporting table and the like.

[Radiographic-Image Capturing Device]

Figure 1:
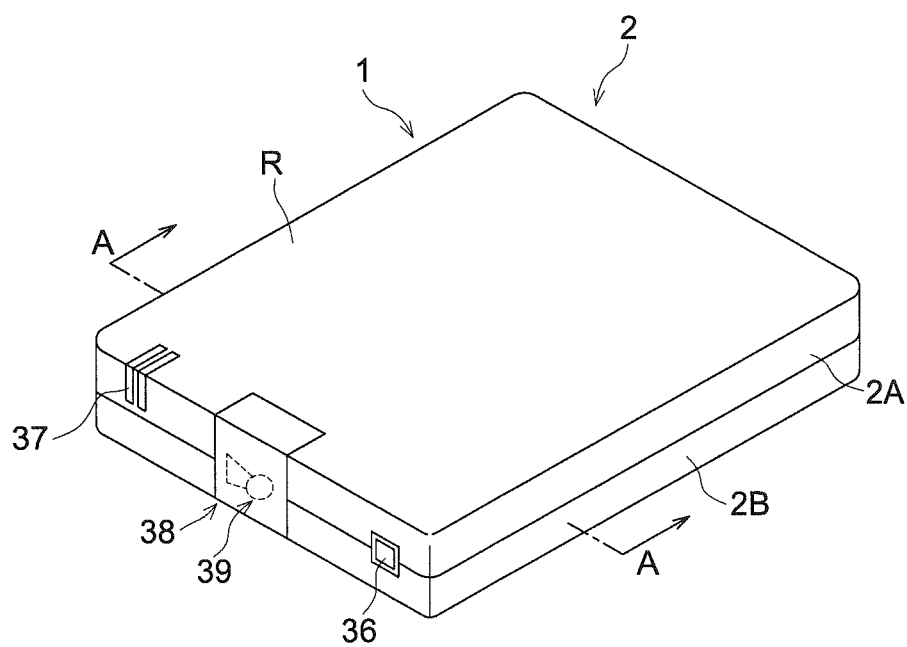
FIG. 1 is a perspective view showing the radiographic-image capturing device relating to the present embodiment.
Figure 2:
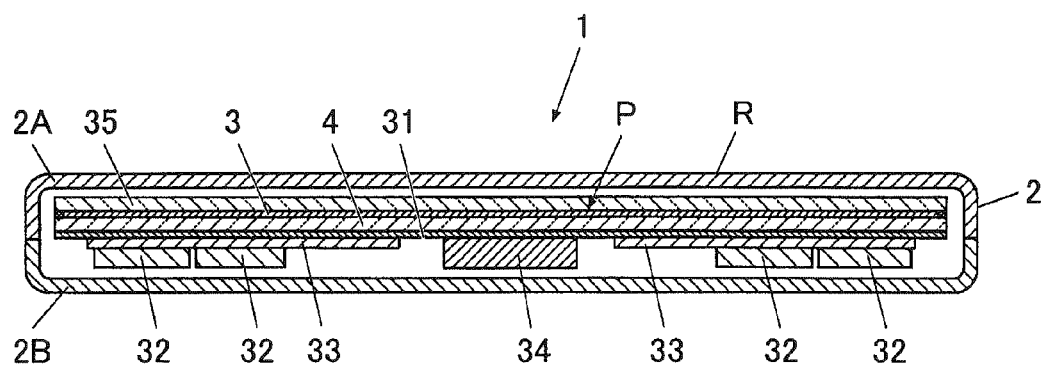
FIG. 2 is a sectional view along the A-A line in FIG. 1.

FIG. 1 is a perspective view of the external appearance of the radiographic-image capturing device relating to the present embodiment, and FIG. 2 is a sectional view along the A-A line in FIG. 1. Radiographic-image capturing device 1 is, as it is shown in FIGS. 1 and 2, composed such that scintillator 3, substrate 4 and the like are stored in casing 2.

At least radiation entering surface R of casing 2 is formed of a material such as a carbon panel, and a plastic which transmits radiation. In FIGS. 1 and 2, a case, in which casing 2 is a so-called Japanese lunch box type, in which the casing 2 is formed of frame plate 2A and back plate 2B, is shown, but a so-called monocoque type, in which casing 2 is integrally formed in a rectangular tube shape, is possible.

As it is shown in FIG. 1, on the side surface of casing 2, there are disposed electric power switch 36, indicator 37 composed of LED or the like, cover member 38 which is designed to be openable and closable for the purpose of exchange of non-illustrated battery 41 (refer to FIG. 7, which will be described later), or the like. In the present embodiment, on the side surface of cover member 38, there is embedded antenna device 39, which is a transfer means to wirelessly transfer image data or the like to an external device such as console 58, which will be described later (refer to FIG. 18). It is also possible to make a constitution so that image data or the like are transferred in a wired system to the external device, and in such the case, for example, as a transfer means, a connecting terminal or the like is arranged on the side surface or the like of radiographic-image capturing device 1 to make a connection by putting in a cable or the like.

As it is shown in FIG. 2, in the interior of casing 2, support base 31 is disposed through a non-illustrated lead thin plate or the like in the downward of substrate 4, and PCB substrate 33 on which electronic part 32 or the like is disposed, cushioning member 34, and the like are installed on support base 31. In the present embodiment, on radiation entering surface R side of substrate 4 and scintillator 3, there is disposed glass substrate 35 to protect them.

Scintillator 3 is pasted to detecting unit P, which will be described later, of substrate 4. As scintillator 3, there is used a device in which, for example, a phosphor is a main component, and, when the device receives entering radiation, the device converts the radiation into electromagnetic waves of wavelength of 300 to 800 nm, that is, an electromagnetic wave centering on a visible light, and then, output it.

Figure 3:
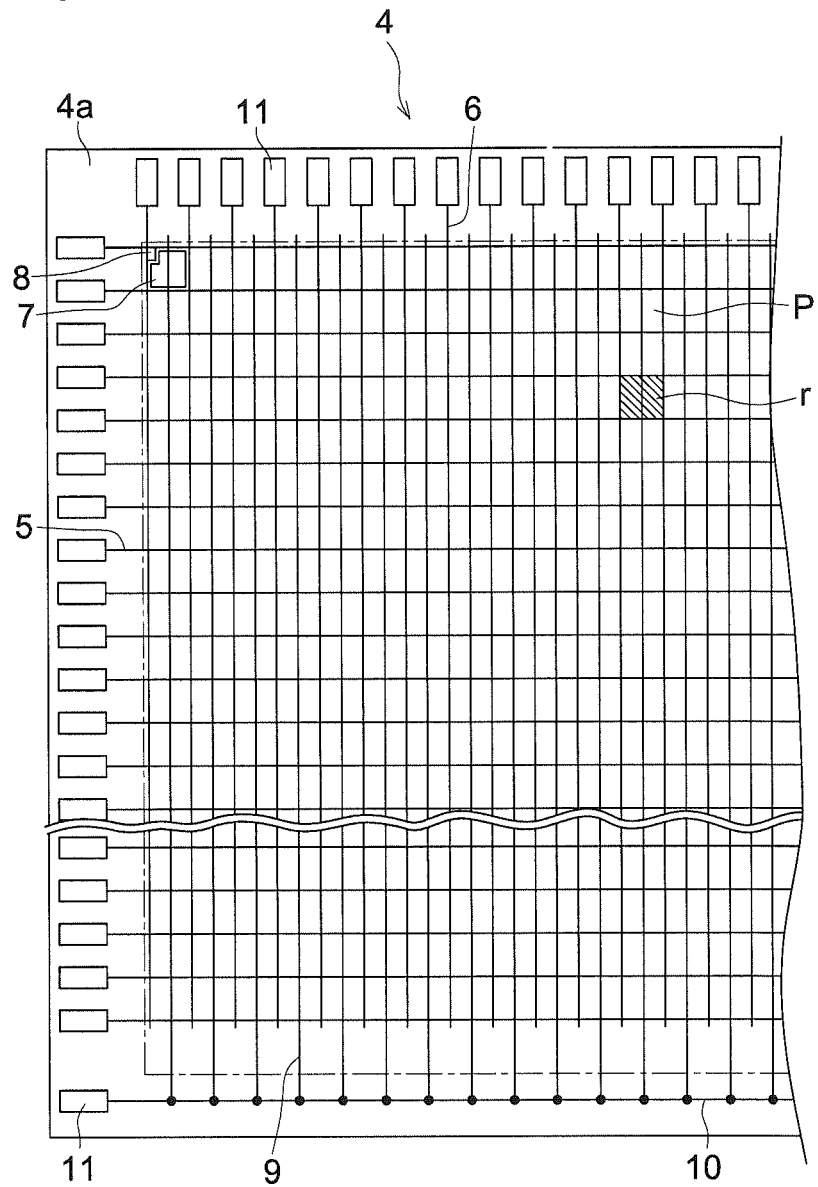
FIG. 3 is a plan view showing a composition of the substrate of the radiographic-image capturing device.

In the present embodiment, substrate 4 is composed of a glass substrate, and, as it is shown in FIG. 3, on surface 4a of the side of substrate 4 facing to scintillator 3, a plurality of scanning lines 5 and a plurality of signal lines 6 are disposed so as to intersect with each other. In each of small areas r partitioned by a plurality of scanning lines 5 and a plurality of signal lines 6 on surface 4a of substrate 4, each of radiation detection elements 7 is disposed.

Total area r in which a plurality of radiation detection elements 7, which were arranged two-dimensionally at each of small areas r partitioned by scanning lines 5 and signal lines 6, are arranged, that is, the area indicated by a dashed-dotted line in FIG. 3, is referred to as detecting unit P.

In the present embodiment, a photodiode is used as radiation detection element 7, but, other than that, for example, a phototransistor or the like may be used. Each radiation detection element 7 is, as it is shown in FIG. 3 and an enlarged FIG. 4, connected with source electrode 8s of TFT 8, a switching means. In addition, drain electrode 8d of TFT 8 is connected with signal line 6.

When an ON voltage is applied to connected scanning line 5, and thereby an ON voltage is applied to gate electrode 8g by scanning driving means 15, which will be described later, TFT 8 becomes an ON state to release electric charges which were generated and accumulated in radiation detection element 7 to signal line 6. Further, when an OFF voltage is applied to connected scanning line 5, and thereby an OFF voltage is applied to gate electrode 8g, TFT 8 becomes an OFF state to stop releasing electric charges from radiation detection element 7 to signal line 6, and thereby retains and accumulates the charges generated in radiation detection element 7 in radiation detection element 7.

Hereinafter, structures of radiation detection element 7 and TFT 8 in the present embodiment will be briefly described with reference to the sectional view shown in FIG. 5. FIG. 5 is a sectional view along the X-X line in FIG. 4.

On surface 4a of substrate 4, there is formed gate electrode 8g of TFT 8 made of aluminum, chromium, or the like or the like by being integrally laminated with scanning line 5, and the upper part of gate electrode 8g, which is located on gate insulating layer 81 composed of silicon nitride ($SiN_x$) or the like and laminated on gate electrode 8g and surface 4a, source electrode 8s, which is connected with first electrode 74 of radiation detection element 7 through semiconductor layer 82 composed of hydrogenated amorphous silicon (a-Si), and drain electrode 8d, which is integrally formed with signal line 6, are laminated and formed.

Source electrode 8s and drain electrode 8d are separated by first passivation layer 83 composed of silicon nitride ($SiN_x$) or the like, and first passivation layer 83 covers both electrodes 8s and 8d from the upper side. Between semiconductor layer 82 and source electrode 8s or drain electrode 8d, each of ohmic contact layers 84a and 84b, which are formed in n-type by doping group VI element into hydrogenated amorphous silicon, is laminated. TFT 8 is formed in the above manner.

In the part of radiation detection element 7, on insulating layer 71, which is integrally formed with above gate insulating layer 81 on surface 4a of substrate 4, aluminum, chromium, or the like is laminated to form auxiliary electrode 72, and further, on auxiliary electrode 72, first electrode 74 composed of aluminum, chromium, molybdenum, or the like is laminated by sandwiching insulating layer 73 which is integrally formed with above first passivation layer 83. First electrode 74 is connected with source electrode 8s of TFT 8 through hole H formed in first passivation layer 83.

On first electrode 74, n layer 75, which is formed in n-type by doping group VI element into hydrogenated amorphous silicon, i layer 76, which is a conversion layer formed of hydrogenated amorphous silicon, and p layer 77, which is formed in p-type by doping group III element into hydrogenated amorphous silicon, are formed by laminating them in the order of increasing.

When radiation enters from radiation entering surface R of casing 2 of radiographic-image capturing device 1, the radiation is converted into electromagnetic waves such as a visible light by scintillator 3, and then, the converted electromagnetic waves are irradiated from the upper side of the figure, the electromagnetic waves reach i layer 76 of radiation detection element 7 to generate electron-hole pairs in i layer 76. Radiation detection element 7 converts the electromagnetic waves irradiated from scintillator 3 into charges in this way.

Further, on p layer 77, there is laminated second electrode 78, which is made as a transparent electrode such as an ITO, and it is structured so that the irradiated electromagnetic waves reach i layer 76 or the like. In the present embodiment radiation detection element 7 is formed in the manner described above. The order of lamination of p layer 77, i layer 76, and n layer 75 may be reversed. Further, in the present embodiment, as radiation detection element 7, there is described a case where a so-called pin-type radiation detection element is used which, as described above, is formed by laminating p layer 77, i layer 76, and n layer 75 in this order, but the embodiment is not limited to it.

On the upper side of second electrode 78 of radiation detection element 7, there is connected bias line 9 which applies a bias voltage to radiation detection element 7 through second electrode 78. Second electrode 78 of radiation detection element 7, bias line 9, first electrode 74, which is extended to TFT 8 side, first passivation layer 83 of TFT 8, and the like, that is, the upper surface part of radiation detection element 7 and TFT 8, are covered with second passivation layer 79 composed of silicon nitride ($SiN_x$) or the like from the upper side thereof.

Figure 4:
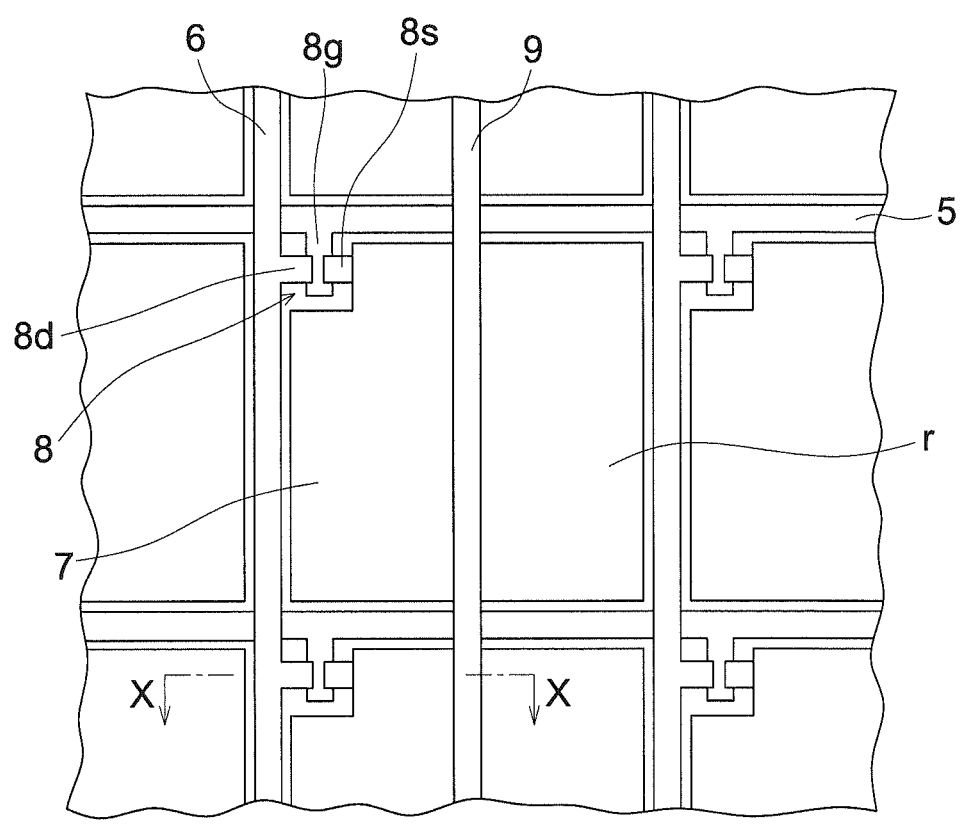
FIG. 4 is an enlarged view showing a composition of the radiation detection element, TFT, and the like formed in a small area on the substrate of FIG. 3.
Figure 5:
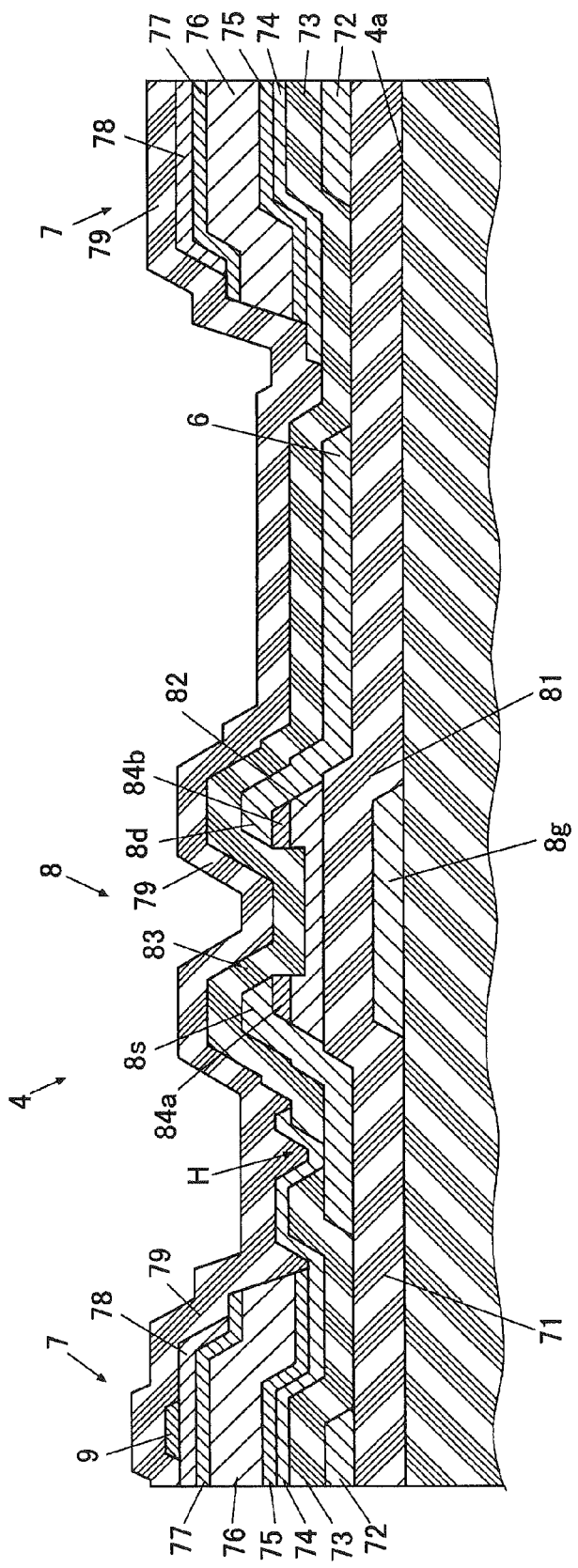
FIG. 5 is a sectional view along the X-X line in FIG. 4.

As is shown in FIGS. 3 and 4, in the present embodiment, one piece of bias line 9 is connected with a plurality of radiation detection elements 7, each of which is arranged in a line, and each bias line 9 is disposed parallel to each signal line 6. Each bias line 9 is banded together with connection 10 at the outside of detecting unit P of substrate 4.

Figure 6:
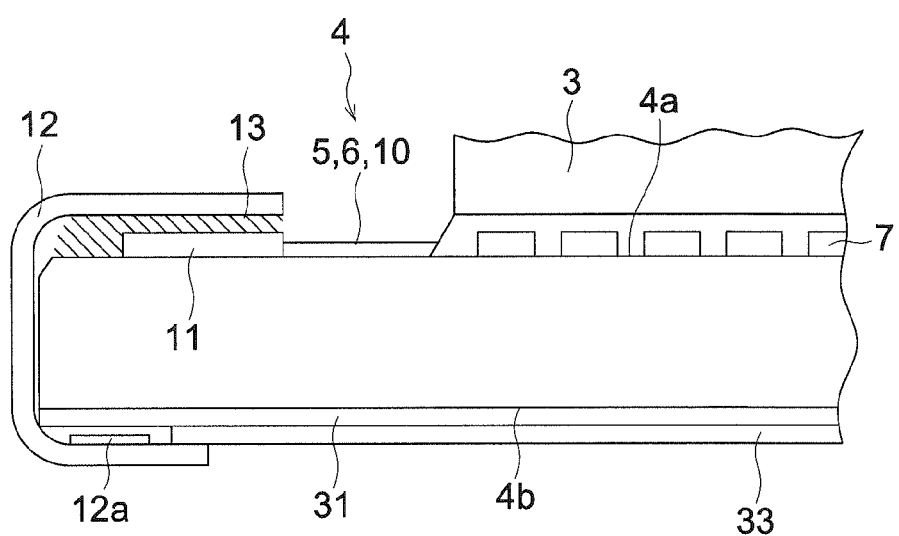
FIG. 6 is a side view describing the substrate on which a COF, a PCB substrate and the like are installed.

In the present embodiment, as is shown in FIG. 3, each scanning line 5, each signal line 6, and connection 10 of bias lines 9 are connected with input-output terminal (also referred to as a pad) 11 which is disposed near the end edge of substrate 4. COF (chip on film) 12, in which chips such as gate IC 12*a*, which constitutes gate driver 15*b* of scanning driving means 15, which will be described later, is connected with each input-output terminal 11, as is shown in FIG. 6, through anisotropic conductive material 13 such as an anisotropic conductive film, and an anisotropic conductive paste.

COF 12 is configured so that COF 12 is put around reverse face 4*b* side of substrate 4, and is connected with above-described PCB substrate 33. In this way, substrate 4 of radiographic-image capturing device 1 is formed. In FIG. 6, illustration of parts such as electronic part 32 are omitted.

Figure 7:
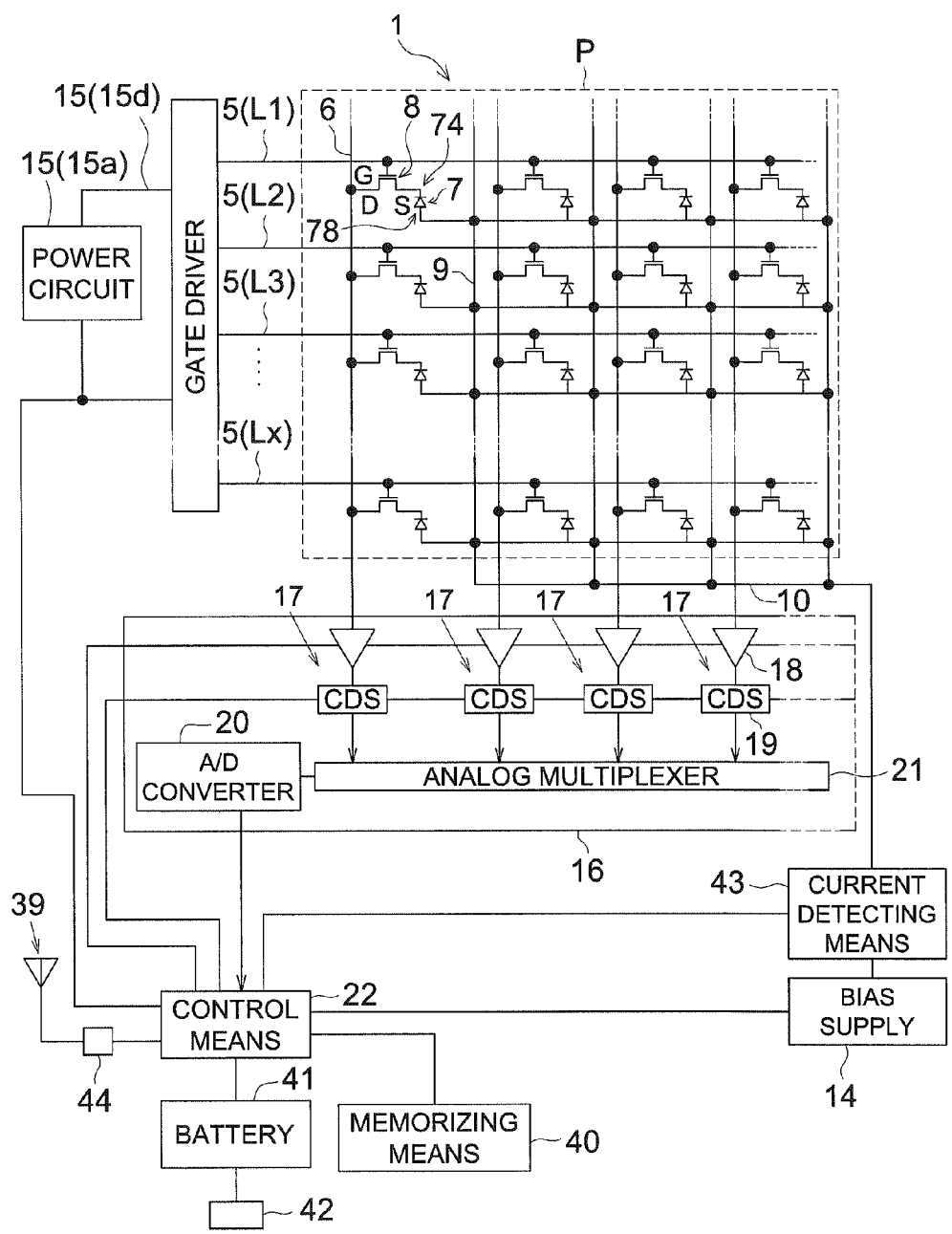
FIG. 7 is a block diagram representing an equivalent circuit of the radiographic-image capturing device.

Hereinafter, the circuit configuration of radiographic-image capturing device 1 will be described. FIG. 7 is a block diagram representing an equivalent circuit of radiographic-image capturing device 1 relating to the present embodiment, and FIG. 8 is a block diagram representing an equivalent circuit of one pixel composing detecting unit P.

As is described above, in each of radiation detection elements 7 of detecting unit P of substrate 4, bias line 9 is connected with each of second electrodes 78 of each of radiation detection elements 7, and each of bias lines 9 is banded together with connection 10 and is connected with bias supply 14. Bias supply 14, through connection 10 and each bias line 9, applies a bias voltage to each second electrode 78 of each radiation detection element 7. In addition, bias supply 14 is connected with control means 22, which will be described later, and control means 22 controls the bias voltage which is applied from bias supply 14 to each of radiation detection elements 7.

In the present embodiment, there is arranged current detecting means 43, which detects the amount of current flowing through connection 10 (bias line 9). As it was described above, when radiation is irradiated on radiographic-image capturing device 1, electron-hole pairs are produced in i layer 76 (refer to FIG. 5) of each of radiation detection elements 7, which then flow out to bias line 9 and connection 10, and thereby, current flows in connection 10 and the like. Current detecting means 43 is designed to be able to detect initiation and termination of irradiation of radiation by detecting increase and decrease of current flowing through connection 10. In the present invention, current detecting means 43 may not necessarily be installed.

Figure 8:
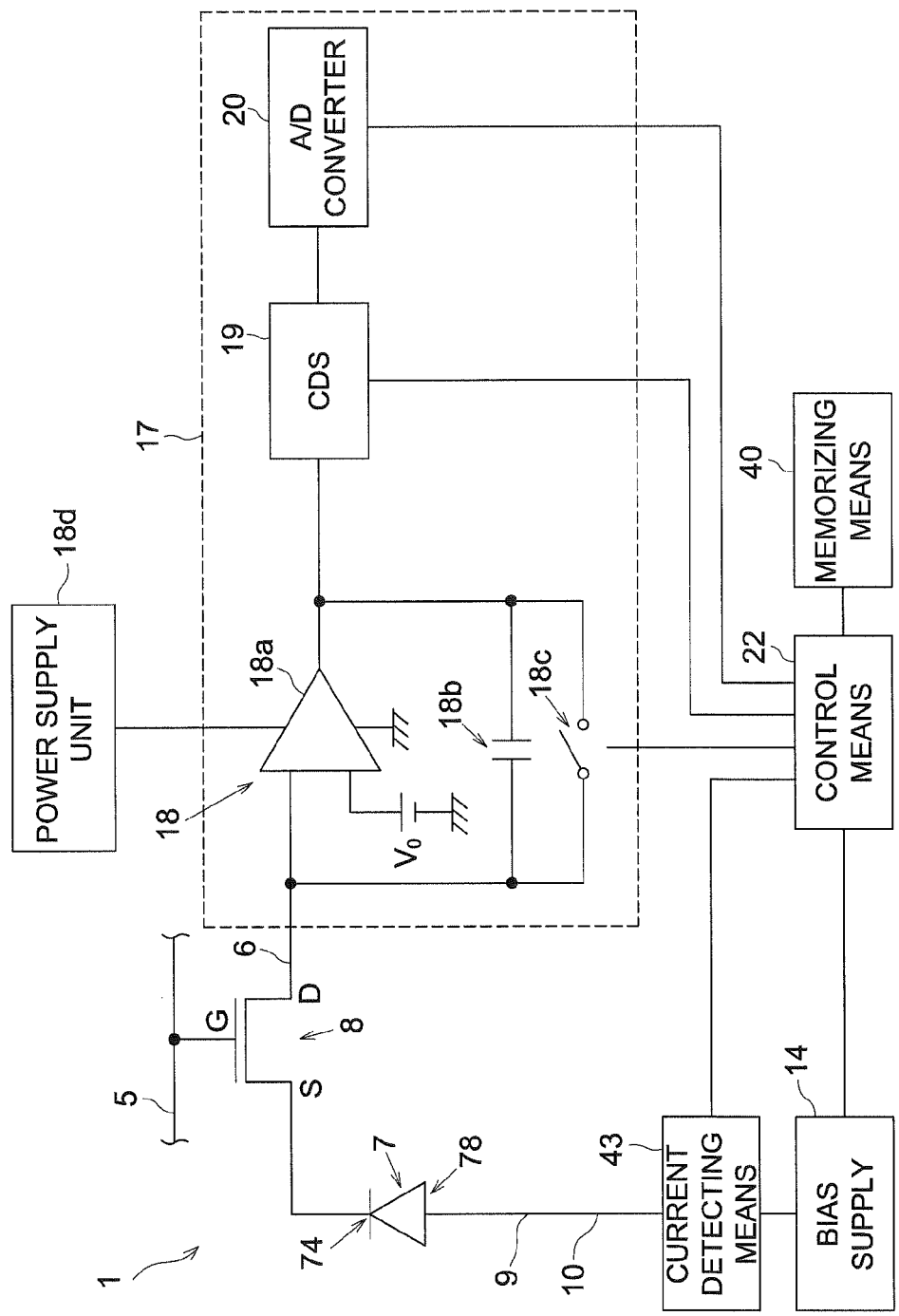
FIG. 8 is a block diagram representing an equivalent circuit of one pixel composing a detecting unit.

As are shown in FIGS. 7 and 8, in the present embodiment, as it is also shown that bias line 9 is, through second electrode 78, connected with p layer 77 side (refer to FIG. 5) of radiation detection element 7, a voltage lower than that applied to first electrode 74 side of radiation detection element 7 as a bias voltage (that is, a so-called reverse bias voltage), through bias line 9, is applied to second electrode 78 of radiation detection element 7 from bias supply 14.

First electrode 74 of each radiation detection element 7 is connected with source electrode 8*s* (which is given as S in FIGS. 7 and 8) of TFT 8, and each gate electrode 8*g* (which is given as G in FIGS. 7 and 8) of each TFT 8 is connected with each of lines L1 to Lx of scanning line 5 extending from gate driver 15*b* of scanning driving means 15, which will be described later. Each drain electrode 8*d* (which is given as D in FIGS. 7 and 8) of each TFT is connected with each signal line 6.

Scanning driving means 15, in the present embodiment, is provided with power circuit 15*a*, which supplies an ON voltage and an OFF voltage to gate driver 15*b*, and gate driver 15*b*, which switches between an ON state and an OFF state of each TFT 8 by switching a voltage applied to each of lines L1 to Lx of scanning line 5 between an ON voltage and an OFF voltage. In the present embodiment, gate driver 15*b* is formed in a way that a plurality of above-described gates IC 12*a* are arranged in juxtaposition to one another.

Each of signal lines 6 is connected with each of read-out circuits 17, which are formed in read-out IC 16. In read-out IC 16, there is arranged one read-out circuit 17 per signal line 6.

Read-out circuit 17 is composed of amplifying circuit 18, correlated double sampling circuit 19, analog multiplexer 21, and A/D converter 20. In FIGS. 7 and 8, correlated double sampling circuit 19 is given as CDS. In FIG. 8, analog multiplexer 21 is omitted.

In the present embodiment, amplifying circuit 18 is constituted of a charge amplifying circuit, and is constituted in a way that each of condenser 18*b* and charge resetting switch 18*c* is connected in parallel with operation amplifier 18*a*. In addition, power supply unit 18*d* for supplying electric power to amplifying circuit 18 is connected with amplifying circuit 18.

Signal line 6 is connected with a reverting input terminal at the input side of operation amplifier 18*a* of amplifying circuit 18, and reference potential $V_0$ is applied to a non-reverting input terminal at the input side of amplifying circuit 18. Reference potential $V_0$ is set at an appropriate value, and, in the present embodiment, for example, zero volt is applied.

Charge resetting switch 18*c* of amplifying circuit 18 is connected with control means 22, which will be described later, and ON/OFF is controlled by control means 22. When TFT 8 of radiation detection elements 7 is made an ON state with charge resetting switch 18*c* being in an OFF state during read-out processing of image data from each radiation detection elements 7 (that is, when an ON voltage for signal read-out is applied to gate electrode 8*g* of TFT 8 through scanning line 5), charges released from aforesaid radiation detection element 7 flow into condenser 18*b* and are accumulated, and thereby a voltage value corresponding to the accumulated amount of charges is output from the output side of operation amplifier 18*a*.

In this way, amplifying circuit 18, according to the amount of charges output from each radiation detection element 7, outputs a voltage value to convert charge into voltage. Further, when charge resetting switch 18*c* is turned ON, the input side and output side of amplifying circuit 18 are short-cut, and then charges accumulated in condenser 18*b* are released, whereby amplifying circuit 18 is reset. Further, it is also possible to constitute amplifying circuit 18 so as to output current according to charges output from radiation detection element 7.

During the read-out processing of image data from each radiation detection element 7, the output voltage value, in which charges are read-out from each radiation detection element 7, which charges are then converted into voltage at amplifying circuit 18, is subjected to sampling processing at correlated double sampling circuit 19 to be output downstream as image data. Then, the image data of each radiation detection element 7 output from correlated double sampling circuit 19 are transmitted to analog multiplexer 21 (refer to FIG. 7), which data are then successively transmitted from analog multiplexer 21 to A/D convertor 20. Then, the above data are successively converted into digital image data by A/D converter 20, which are then output in memorizing means 40, to be successively stored.

In the present embodiment, at a time when read-out of image data from each radiation detection element 7 is processed, the read-out processing like the above of image data from each radiation detection element 7 is carried out, while each of lines L1 to Lx of scanning line 5 to which an ON voltage is applied is successively switched.

In the present embodiment, it is configured so that, for example, 128 signal lines 6 are processed by one read-out IC 16. Namely, one read-out IC 16 is formed of, corresponding to each of signal lines 6, 128 read-out circuits 17 (that is, amplifying circuit 18, correlated double sampling circuit 19, and the like), one analog multiplexer 21, one A/D converter 20, and the like.

If, for example, the number of signal lines 6 is 2048, 16 read-out ICs 16 (2048÷128=16) are arranged in parallel to form a read-out section. Hereinafter, description is made assuming that the number of read-out circuits 17 formed in one read-out IC 16, that is, the number of signal lines 6 connected with one read-out IC 16, is 128, and the total number of signal lines 6 is 2048, but the present invention is obviously not limited to the case.

Figure 9:
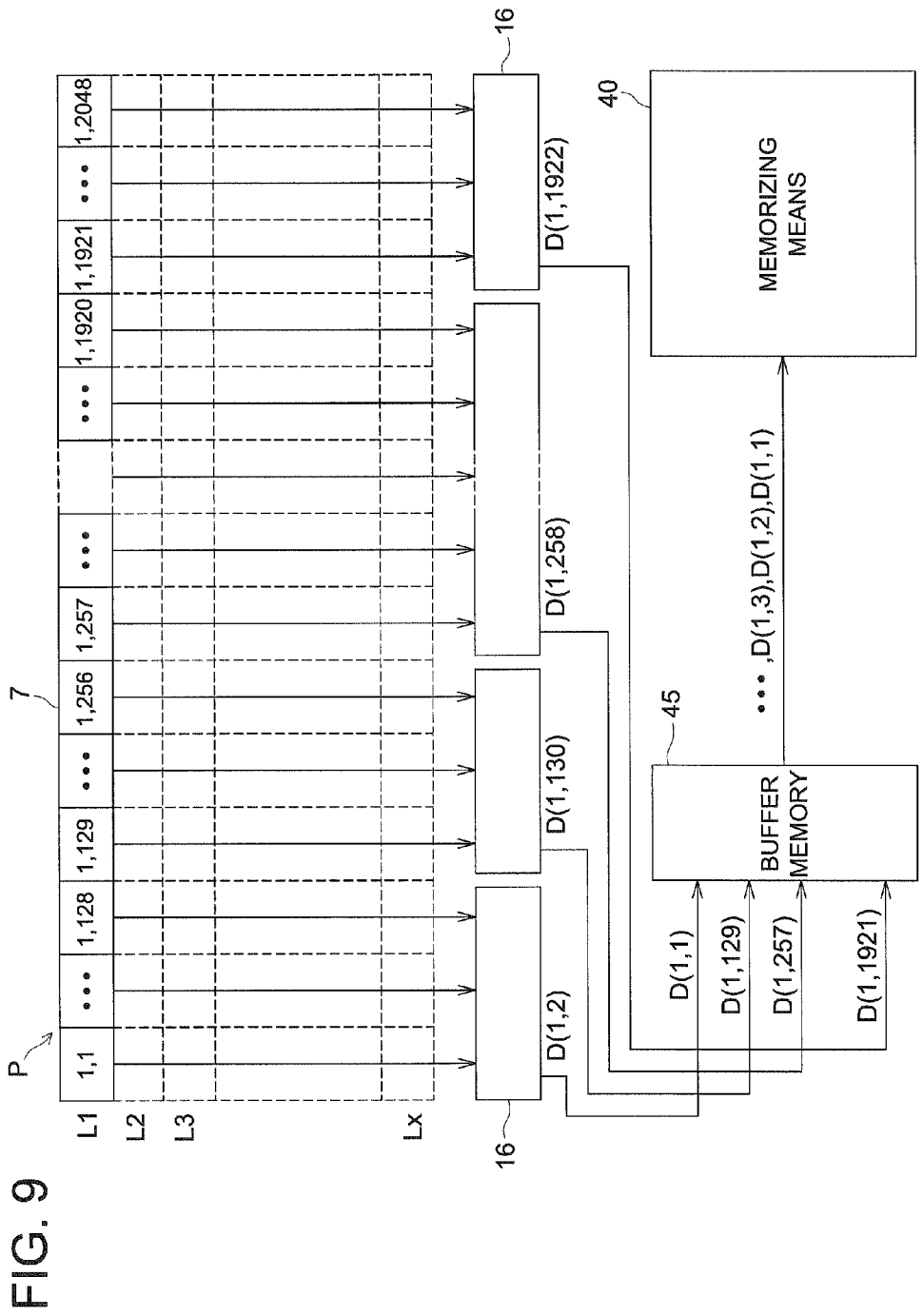
FIG. 9 is a figure describing a state in which image data read out all at once from radiation detection element by each read-out IC are accumulated in the buffer memory, after which the order of the image data are rearranged, and then, the image data are transferred to a memorizing means.

As it is shown in FIG. 9, at a time of read-out processing of image data, when an ON voltage is applied, for example, to line L1 of scanning line 5, image data are all at once read out from each of radiation detection elements (1, 1) to (1, 2048), which are then sent in parallel to each of read-out IC 16.

Then, the conversion of charge into voltage and the like are carried out at each read-out circuit 17 (which illustration is omitted in FIG. 9) of each read-out IC 16, and then each of 128 image data, which were transmitted in parallel, is successively subjected to serial transmission to A/D converter 20 (not illustrated) by each analog multiplexer 21 (not illustrated) in each read-out IC 16, and then digitized image data are temporarily accumulated in buffer memory 45 from A/D converter 20.

Namely, if each of image data corresponding to each of radiation detection elements (x, y) is written as D (x, y), first of all, from each of read-out ICs 16, each of image data D (1, 1), D (1, 129), D (1, 257), . . . , D (1, 1921) is transmitted to be accumulated in buffer memory 45, and subsequently, each of image data D (1, 2), D (1, 130), D (1, 258), . . . , D (1, 1922) is transmitted to be accumulated in buffer memory 45.

Then, once each of image data D (1, 1) to D (1, 2048) from each of radiation detection elements (1, 1) to (1, 2048), which are connected with line L1 of scanning line 5, is accumulated, each of image data D is rearranged in the order of image data D (1, 1), D (1, 2), D (1, 3), D (1, 4), . . . , and is then successively transmitted to memorizing means 40 to be stored.

When read-out processing of each of image data D (1, 1) to D (1, 2048) from each of radiation detection elements (1, 1) to (1, 2048), which are connected with line L1 of scanning line 5 is completed, subsequently, the line of scanning line 5, to which an ON voltage is applied, is switched to L2. Then, in a similar way, each of image data D (2, 1) to D (2, 2048) is transmitted to buffer memory 45 according to each read-out IC 16, and then rearranged, after which each of the data is successively transmitted to memorizing means 40 to be stored.

Then, the above-described read-out processing and storing processing in memorizing means 40 are successively repeated for each of lines L1 to Lx of scanning line 5, and thereby read-out processing of image data D from all radiation detection elements 7 are carried out.

The above rearrangement of image data D can be carried out, even if any non-illustrated external devices transmitting image data D are used, if usually image data D are transmitted in the order of D (1, 1), D (1, 2), D (1, 3), D (1, 4), . . . , and therefore the above rearrangement of image data D is processing to rearrange the image data D in the above order and store them for many uses at a step of storing image data D in memorizing means 40.

Therefore, in the case where the transferring order and the like of each of image data D from radiographic-image capturing device 1 to an external device can be made in advance, it is possible to constitute so that a rearrangement of image data D is made according to the above arrangement.

If arrangement is made in advance that each of image data D is transferred from radiographic-image capturing device 1 to an external device in, for example, an output order from each read-out IC 16, that is, in the order of D (1, 1), D (1, 129), . . . , D (1, 1921), D (1, 2), D (1, 130), . . . , D (1, 1922), . . . , it becomes possible to directly send successively, without going through buffer memory 45, image data D outputted from each of read-out IC 16 to memorizing means 40 to store them.

Further, when a rearrangement of image data D is made in such a way described above, it is also possible to constitute so that a rearrangement of image data D is carried out at a time of reading out each of image data D from memorizing means 40, not at a time of storing each of image data D in memorizing means 40.

In the present embodiment, there is described a case where, after each image data D, which were read out from each radiation detection element 7, is temporarily stored in memorizing means 40, compression processing is carried out for each of image data at a time of transferring the stored data from radiographic-image capturing device 1 to a non-illustrated external device, but it is also possible to constitute so that each of image data D, which were read out from each radiation detection element 7, is not stored in memorizing means 40, or, in parallel with storing it in memorizing means 40, is directly transferred after each of image data D is, as different processing, compressed.

Control means 22 is composed of a CPU (central processing unit); a computer, in which a ROM (read only memory), a RAM (random access memory), an input-output interface, and the like are connected with a bus; FPGA (field programmable gate array), or the like, all of which are not illustrated in the figure. Control means 22 may also be composed of an exclusive control circuit. Then, control means 22 controls operation or the like of each member of radiographic-image capturing device 1. In addition, as shown in FIG. 7 or in other figures, memorizing means 40, which is composed of a DRAM (dynamic RAM), or the like is connected with control means 22.

In the present embodiment, control means 22 is connected with above-described antenna device 39, and further, connected with battery 41 to supply electric power to each of members such as detecting unit P, scanning driving means 15, read-out circuit 17, memorizing means 40, and bias supply 14. In addition, battery 41 is attached with connection terminal 42 used for charging battery 41 by supplying power from a non-illustrated charging equipment such as a cradle to battery 41.

As it was described above, control means 22 performs various processing such as setting a bias voltage to apply from bias supply 14 to each radiation detection element 7 by controlling bias supply 14, controlling ON/OFF of charge resetting switch 18c of amplifying circuit 18 of read-out circuit 17, or transmitting pulse signals to correlated double sampling circuit 19, to controls ON/OFF of the sample holding function.

Further, control means 22, at a time of reset processing of each radiation detection element 7, or at a time of reading out of image data D from each radiation detection element 7 after capturing radiation images, transmits pulse signals to scanning driving means 15 to switch, between an ON voltage and an OFF voltage, a voltage applied from scanning driving means 15, through each scanning line 5, to gate electrode 8$g$ of each TFT 8.

In the present embodiment, register section 44 provided with at least two buffer registers is connected with control means 22, and a compression means and a means for preparing thinned-out data are formed of control means 22 and resister section 44.

In the present embodiment, register section 44 is integrally arranged at FPGA, which constitutes control means 22. In the case where control means 22 is constituted of a computer comprising a CPU or the like, it is also possible to configure so that an existing resister is used as resister section 44. Further, in the present embodiment, two buffer registers are disposed at resister section 44, but it is also possible to configure to arrange one buffer register as it will be described later, or three or more buffer registers may be arranged.

Hereinafter, there will be described compression processing of image data D relating to the present invention by control means 22 as a compression means.

In the present embodiment, as it will be described later, there will be described a case where, after difference data ΔD of image data D which was read-out from memorizing means 40 was subjected to compression processing, the compressed difference data ΔD are not stored in memorizing means 40 without any change, but are transferred in a wireless way from antenna device 39 to an external equipment, it is possible to configure so that the compressed difference data ΔD are stored in memorizing means 40 of radiographic-image capturing device 1.

In the following paragraphs, characteristics of the compression processing of image data relating to the present invention will be described.

As it was described above, in the case where it is configured so that each of image data D is stored in memorizing means 40 in the order of D (n, 1), D (n, 2), D (n, 3), D (n, 4), . . . for each line Ln of scanning line 5, when reading out each of image data from memorizing means 40, if each of image data D is constituted to be read out in the same order, each of image data can be easily read out.

Figure 10:
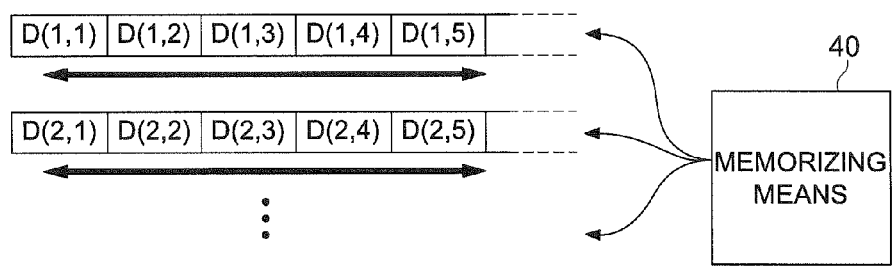
FIG. 10 is a figure describing a state in which compression processing is carried out for each of image data which are formed in line in the scanning direction in the conventional compression processing of image data.

Therefore, in the conventional compression processing of image data D, in general, as it is shown in FIG. 10, every time image data D (n, 1), D (n, 2), D (n, 3), D (n, 4), . . . , of each line Ln of scanning line 5 is read out from memorizing means 40, each of image data D is compressed. Namely, compression processing of image data D is carried out for each of image data D forming line in the scanning direction (that is, each of image data D output from each radiation detection element 7 connected with the same scanning line 5), and moreover, the compression processing of image data D is carried out for each of lines L1 to Lx of scanning line 5. The arrows written under each of image data D in FIG. 10 indicate the direction in which compression processing is carried out, that is, indicate the scanning line direction in this case.

Figure 11:
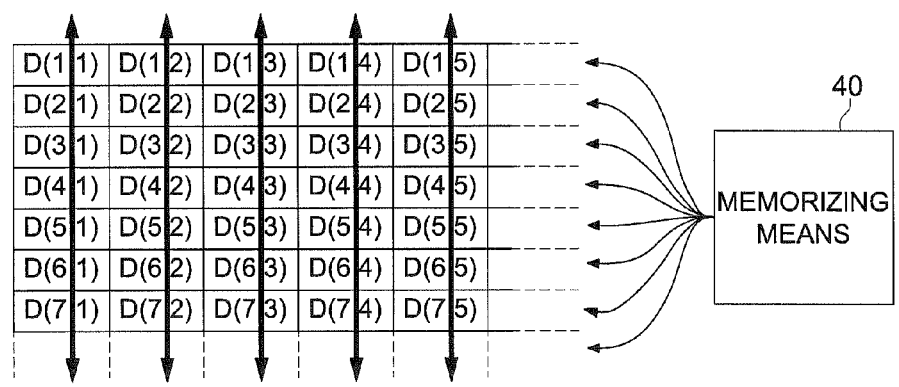
FIG. 11 is a figure describing a state in which compression processing is carried out for each of image data in the signal line direction in the compression processing of image data of the present invention.

In contrast, in the compression processing of image data D of the present invention, as it is shown in FIG. 11, for image data D (n, 1), D (n, 2), D (n, 3), D (n, 4), . . . , of each line Ln of scanning line 5, the compression processing is carried out for each of image data D in the direction of signal line which is arranged so as to be perpendicular to scanning line 5, that is, each of image data D outputted from each radiation detection element connected with the same signal line 6. Namely, it is configured so that the above compression processing of image data D is carried out for each signal line 6. Each arrow in the vertical direction on each of image data in FIG. 11 indicates the direction in which the compression processing is carried out, that is, the signal line direction in this case.

In the compression processing of image data D, it is also possible to configure that each of image data D in the signal line direction is compressed without any changes. But, since image data D of the present embodiment are finely divided into gradations to an extent comparable to an analogue image in which the conventional silver halide film is used, a dynamic range of data values in which each of image data D can take becomes very large.

For example, if the number of gradations of image data D is 30 thousand, each of image data D can take each of data values between 0 and 30,000. Then, for example, if a compression method of image data D such as Huffman encoding, which will be described later, is used, compression ratio Rc of image data D may not necessarily become an excellent value.

On the other hand, in the case of a radiation image, it is known that when differences between image data D adjoining to each other are calculated, the distribution of the differences becomes relatively narrow. Then, traditionally, for image data D (n, 1), D (n, 2), D (n, 3), D (n, 4), . . . , of each line Ln of scanning line 5, which were read out from memorizing means 40, or from each radiation detection element 7, differences between image data D adjoining to each other are calculated to prepare difference data, and then, compression processing to the difference data is generally carried out.

Even in radiographic-image capturing device 1 of the present embodiment, there is also adopted this method of compression processing to the difference data which was prepared by calculating differences between image data D adjoining to each other. However, as it was described above, in the present embodiment, it is constituted in such a way that, for each of image data D in the signal line direction, that is, each of image data D (1, m), D (2, m), D (3, m), D (4, m), . . . , outputted from each radiation detection element connected with the same signal line 6 (refer to FIG. 11), differences between image data D adjoining to each other are calculated to prepare difference data ΔD, and then compression processing is carried out for the difference data ΔD.

Figure 12:
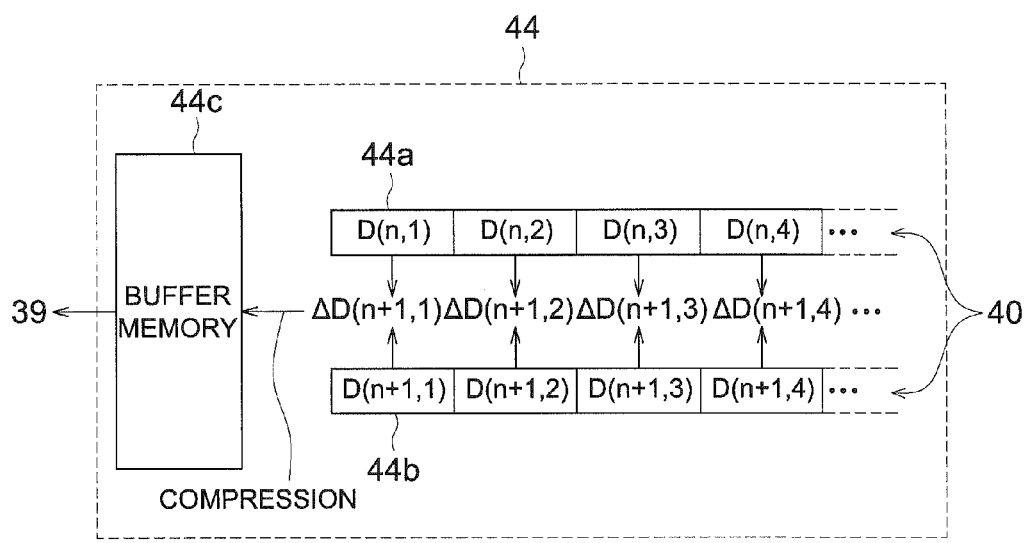
FIG. 12 is a figure describing a composition of the registration section, and a method for preparing difference data between image data which are adjacent to each other in the signal line direction and are connected with the same signal line of the present embodiment.

Specifically, in the present embodiment, as it is shown in FIG. 12, in resister section 44, at least two buffer registers 44$a$ and 44$b$ are arranged, and there is also arranged buffer memory 44$c$, which temporarily stores each of compressed difference data ΔD before transferred to an external device through antenna device 39.

Control means 22, at a time of compression processing of image data D (difference data ΔD), reads out, from memorizing means 40, each of image data D (n, 1), D (n, 2), D (n, 3), D (n, 4), . . . , D (n+1, 1), D (n+1, 2), D (n+1, 3), D (n+1, 4), . . . , which were read out from each radiation detection element 7, which is connected with each of lines Ln, and Ln+1 of adjoining scanning lines 5, and forms in line in the scanning direction, and then temporarily accumulates them in each of buffer register 44$a$ and 44$b$.

Then, since image data D having the same address in buffer registers 44$a$ and 44$b$ are image data D outputted from each radiation detection element connected with the same signal line 6, difference data ΔD between image data D of radiation detection elements 7 adjoining in the signal line direction connected with the same signal line 6 is prepared by calculating difference ΔD between image data having the same address (namely, ΔD (n+1, 1), ΔD (n+1, 2), ΔD (n+1, 3), ΔD (n+1, 4), . . . ).

At that time, if a configuration is made such that each of image data D of adjoining two lines and of forming in line in the scanning line direction is read out every time from memorizing means 40 in order to prepare difference data ΔD, a read-out control becomes troublesome.

Therefore, in the present embodiment, when control means 22 calculates difference data ΔD between each of image data D read out from each radiation detection element 7 connected with each of lines Ln and Ln+1 of adjoining scanning line 5, and forms in line in the scanning direction, transfers each of data D (n+1, 1), D (n+1, 2), D (n+1, 3), D (n+1, 4), . . . from buffer register 44*b* to buffer register 44*a*, and then accumulates each of data D (n+2, 1), D (n+2, 2), D (n+2, 3), D (n+2, 4), . . . , which forms in line in the scanning line direction of line Ln+2 of scanning line 5 adjoining to line Ln+1, in empty buffer register 44*b*.

Subsequently, after calculation of difference data ΔD (n+2, 1), ΔD (n+2, 2), . . . , each of image data D (n+2, 1), D (n+2, 2), . . . is transferred from buffer register 44*b* to buffer register 44*a*, and then each of image data D (n+3, 1), D (n+3, 2), . . . is accumulated in buffer register 44*b*. In this way, while translocating each of image data D from buffer register 44*b* to buffer register 44*a*, calculation processing of difference data ΔD between image data D having the same address of buffer registers 44*a* and 44*b* is repeated to successively form difference data ΔD.

In the case of making a configuration as described above, reference data become required to calculate difference data ΔD (1, 1), ΔD (1, 2), ΔD (1, 3), ΔD (1, 4), . . . of each of image data D (1, 1), D (1, 2), D (1, 3), D (1, 4), . . . , which is read out from each radiation detection element 7 connected with the first line L1 of scanning line 5, and forms in line in the scanning direction. Therefore, in the present embodiment, reference data Dc (1), Dc (2), Dc (3), Dc (4), . . . , which were already set, are stored beforehand in a memory such as a ROM.

Figure 13:
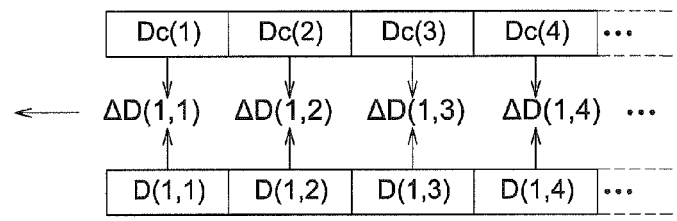
FIG. 13 is a figure describing that difference data from the reference data are calculated regarding each of the image data which were read out from each radiation detection element connected to line L1 of the scanning lines.

Then, control means 22, when calculating each of difference data ΔD (1, 1), ΔD (1, 2), ΔD (1, 3), ΔD (1, 4), . . . , as it is shown in FIG. 13, accumulates reference data Dc (1), Dc (2), Dc (3), Dc (4), . . . , which were read out from the memory, in buffer register 44*a*, and accumulates each of image data D (1, 1), D (1, 2), . . . , which were read out from each radiation detection element 7 connected with line L1 of scanning line 5 read out from memorizing means 40, and forms in line in the scanning direction, in buffer register 44*b*, and then calculates difference ΔD thereof as difference data ΔD (1, 1), ΔD (1, 2), . . . .

At that time, each value of reference data Dc (1), Dc (2), . . . , may be set as an identical one, or may be set as a difference one from each other, and is appropriately set in advance.

Even in the case where only one buffer register 44*a* is arranged in resister section 44, it is possible to make a configuration such that differences of image data D adjoining in the signal direction similar to the above are calculated to form difference data ΔD.

Figure 14A:
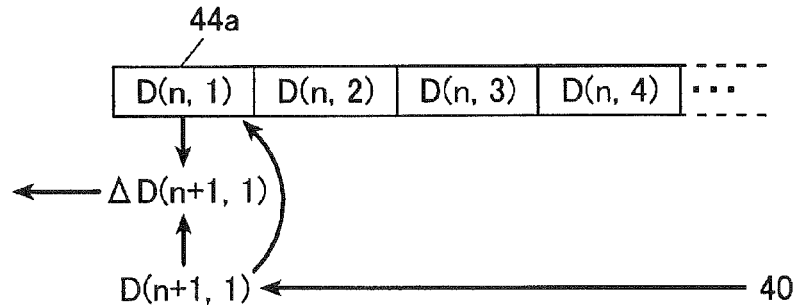
FIGS. 14A to 14 C are figures describing a method for preparing difference data between image data which are adjacent to each other in the signal line direction and are connected with the same signal line using one buffer register.
Figure 14B:
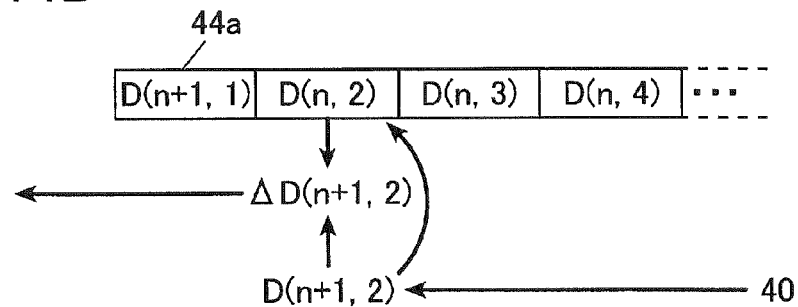
Figure 14C:
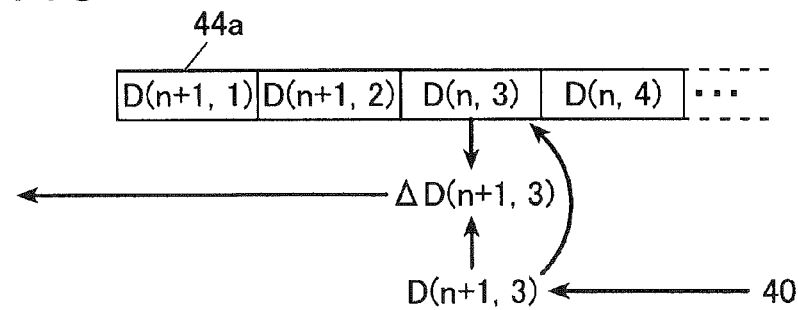

It is assumed that, as they are shown in FIGS. 14A to 14C, among each of image data D, which was read out from each radiation detection element 7 connected with each of adjoining lines Ln and Ln+1 of scanning line 5, and forms in line in the scanning direction, each of image data D (n, 1), D (n, 2), D (n, 3), D (n, 4), . . . , which forms in line in the scanning line direction of line Ln of scanning line 5, is accumulated in buffer register 44*a*.

In the above situation, control means 22 successively reads out, from memorizing means 40, each of image data D (n+1, 1), D (n+1, 2), D (n+1, 3), D (n+1, 4), . . . , which forms in line in the scanning direction of line Ln+1 of adjoining scanning line 5, and, while successively replacing it with each of corresponding imaging data D (n, 1), D (n, 2), D (n, 3), D (n, 4), . . . , accumulates it in buffer register 44*a*, and at that time, the configuration is made so that the replacement is made after calculation of difference data ΔD between corresponding image data D.

When the configuration is made in such a way, even in the case where only one buffer register 44*a* is arranged, it becomes possible to prepare, in the similar manner to the above, difference data ΔD between image data D, which were output from adjoining radiation detection elements 7 connected with the same signal line 6.

Further, each of image data D (n+1, 1), D (n+1, 2), D (n+1, 3), D (n+1, 4), . . . , in which difference data ΔD were prepared in this way, is accumulated in buffer register 44*a* while being replaced, is next replaced by each of image data D (n+2, 1), D (n+2, 2), D (n+2, 3), D (n+2, 4), . . . , which were successively read out from memorizing means 40, while difference data ΔD are successively prepared. Therefore, even in the case where only one buffer register 44*a* is arranged, it becomes possible to carry out easily and continuously preparation processing of each of difference data ΔD.

On the other hand, the present embodiment is configured, as it was described above, so that compression processing is carried out for difference data ΔD prepared in this way.

As it was described above, in the case where the radiographic-image capturing device is used as an image capturing device of the medical image, in which an image of a part of the body of the patient as a subject is captured, and the obtained radiographic image is used for diagnosis or the like as a medical image, it is preferable to adopt the reversible compression method, as an image data compression method, in which compression is carried out so that difference data ΔD (or image data D) before compressed perfectly agree with difference data ΔD (or image data D) after restored.

In the present embodiment, as the reversible compression method, the Huffman encoding method is adopted. Hereinafter, there will be described a case where the compression processing of difference data (or image data D) is carried out using the Huffman encoding method, but the compression method is not necessarily carried out by the Huffman encoding and it is also possible to make a constitution so as to carry out the compression processing of difference data ΔD (or image data D) using other reversible compression methods or the irreversible compression method.

In the present embodiment, in order to carry out the compression processing of difference data ΔD using the Huffman encoding method, Huffman coding table, which was already made for the compression processing, is stored in advance in a memory such as an ROM, and then control means 22 constituting the compression means is configured so as to carry out the Huffman encoding of difference data ΔD with reference to the table when the compression processing is carried out.

In the present embodiment, control means 22, at every time difference data ΔD is formed in the above manner, with reference to the Huffman coding table, allots corresponding Huffman coding Hc for aforesaid difference data ΔD. Namely, each Huffman coding Hc corresponds to each of compressed difference data ΔD. In the data compression using the Huffman coding, as it is well known, the higher the appearance frequency of data, the shorter the Huffman coding Hc being allotted.

Control means 22 temporarily stores each Huffman coding Hc, which was allotted to each of difference data ΔD, in buffer memory 44c (refer to FIG. 12), and successively transfers the allotted coding to the external device through antenna device 39.

In this case, it is configured so that the above external device, to which difference data ΔD are transferred from radiographic-image capturing device 1, is also provided with the same table of Huffman coding Hc, and, at the external device, compressed and transferred difference data ΔD are decompressed with reference to the table at the time of decompression. Further, it is also possible to constitute so that, without preparing difference data ΔD, each of image data D in the signal line direction is compressed without any change, but, in the case of such constitution, it is constituted so that each of radiographic-image capturing device 1 and the external device is provided with the common table of Huffman coding Hc for the compression/decompression of image data D.

As the table of Huffman coding, it may be constituted so as to be provided with only one kind of table, but it may also be constituted so that a plurality kinds of tables are provided, and a table is selected at control means 22, which will be then referred to. For example, in the case where radiographic-image capturing device 1 is used as a medical image capturing device as it was described above, depending on image capturing locations (the chest, the skull, the lumbar spine, or the like) of the patient, who is an image capturing subject, or the image capturing direction thereof (the front, the side, or the like), the image capturing conditions such as the amount of irradiated radiation and irradiation time may often be changed.

For that reason, for each of image capturing conditions including image capturing locations of the patient, who is an image capturing subject, or the image capturing direction thereof, a plurality kinds of tables of Huffman coding used for compression processing are previously provided, and if it is constituted in such a manner that control means 22 selects a table according to the predetermined image capturing conditions, and compression processing of difference data ΔD (or image data D) is carried out by carrying out Huffman encoding of difference data ΔD (or image data D) with reference to the selected table, it becomes possible to further increase compression ratio Rc of difference data ΔD (or image data D) in accordance with image capturing conditions.

In the case of medical image capturing using radiographic-image capturing device 1, image capturing order information, which specifies in advance image capturing locations of the patient, who is an image capturing subject, the image capturing direction thereof, or the like, is often made, and image capturing conditions for radiographic-image capturing device 1 are set by, for example, transferring the image capturing order information or information of the image capturing conditions including image capturing locations, the image capturing direction thereof, or the like, from the external device to radiographic-image capturing device 1, or by an operator, such as a radiation technologist, inputting the image capturing order information or the information of the image capturing conditions into radiographic-image capturing device 1.

It is possible to make a constitution so that correspondence of the image capturing conditions to the table of Huffman coding Hc is commonly made in advance in radiographic-image capturing device 1 and an external device, and, based on the formed image capturing order information, both radiographic-image capturing device 1 and the external device specify a table to be used from image capturing locations, the image capturing direction thereof, or the like in the aforesaid image capturing order information, to use a common table. It is also possible to constitute so that, when transferring Huffman coding Hc as compressed difference data ΔD from radiographic-image capturing device 1 to an external device, information of the number of the table to be used or the like is transferred together with above Huffman coding Hc, and then, at the external device, above Huffman coding Hc is decompressed using a table designated by the information of the number or the like.

Further, it is also possible to constitute so that a table of Huffman coding Hc, which is suitable for the image capturing conditions of the aforesaid radiation image capturing, is transferred from an external device to radiographic-image capturing device 1 at every time a radiographic-image is captured, which table is then stored or rewritten, and control means 22 carries out Huffman encoding of image data D or difference data ΔD with reference to the aforesaid transferred table of Huffman coding Hc, to carry out compression processing.

Next, an action of radiographic-image capturing device 1 relating to the present embodiment will be described.

As it was described above, in the compression processing of image data D or difference data ΔD, which was previously generally carried out, compression processing was carried out, as it was shown in FIG. 10, for image data D (n, 1), D (n, 2), D (n, 3), D (n, 4), . . . , outputted from each of radiation detection elements 7 connected with line Ln of the same scanning line 5, that is, each of image data D, which form in line in the scanning line direction or difference data ΔD between each of image data D which adjoin in the scanning line direction.

Figure 23:
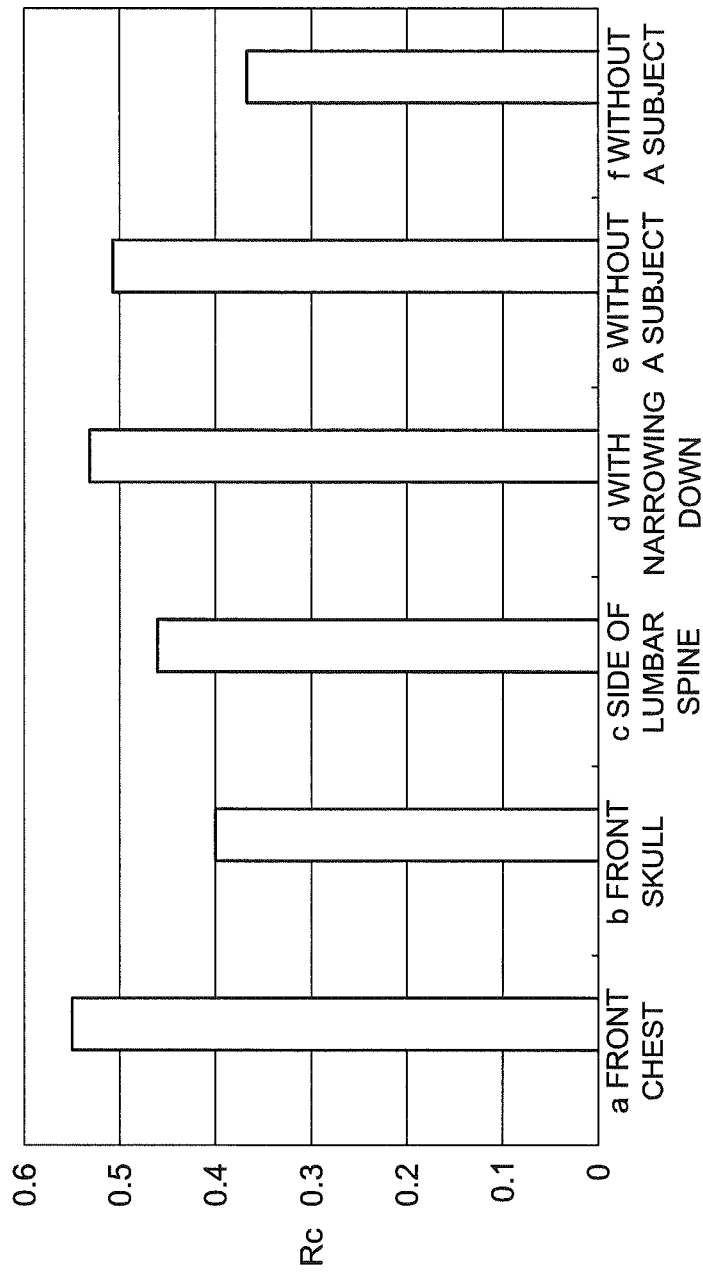
FIG. 23 is a graph indicating each compression ratio in the conventional compression processing in which the difference data are compressed on image data which are formed in line in the scanning direction under each of the conditions of "a" to "f".

In the case where compression processing is carried out in such a way, it was found that there is a case where a relatively large difference is generated in compression ratio Rc of image data D or difference data ΔD depending on, as it is shown in FIG. 23, for example, image capturing locations (the chest, the skull, the lumbar spine, or the like) of the patient, who is an image capturing subject, or the image capturing direction thereof (the front, the side, or the like), or with or without narrowing down, or large or small of the amount of radiation which is uniformly irradiated in the case of no subject.

Figure 15A:
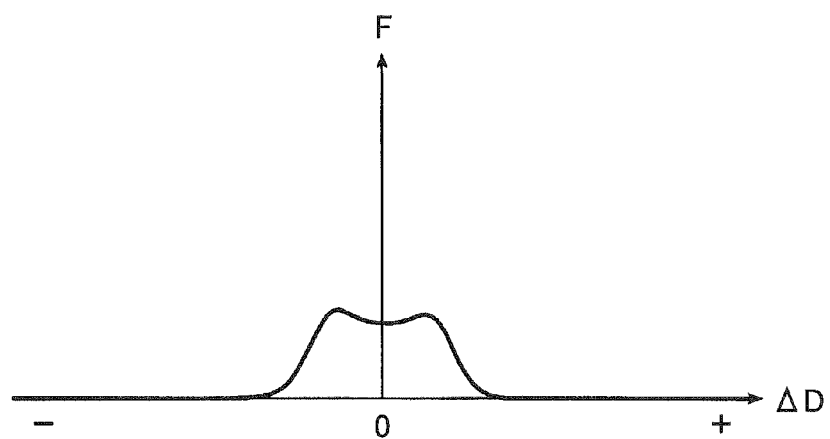
FIG. 15A is a graph showing a distribution of difference data of image data outputted from each radiation detection element connected with the same scanning line when radiation is uniformly irradiated on the device.

In order to clarify the cause that, as it was described above, compression ratio Rc of image data D or difference data ΔD varies and, depending on image capturing conditions such as image capturing locations, compression ratio Rc may significantly decrease, there was calculated each of difference data ΔD of image data D (n, 1), D (n, 2), D (n, 3), D (n, 4), . . . , outputted from each of radiation detection elements (n, 1), (n, 2), (n, 3), (n, 4), . . . , which were connected with line Ln of same scanning line 5, when radiation was uniformly irradiated on radiographic-image capturing device 1, resulting in the distribution of difference data ΔD as it is shown in FIG. 15A. The vertical axes of FIG. 15A, as well as FIG. 15B and FIGS. 16A and 16B indicate appearance frequency F of above difference data ΔD.

Regardless that each of radiation detection elements (n, 1), (n, 2), (n, 3), (n, 4), . . . , which were connected with line Ln of same scanning line 5, receives irradiation of radiation of the same amount, or receives irradiation of electromagnetic waves of the same intensity, which were converted by scintillator 3 which received irradiation of radiation of the same amount, it is found, as it is shown in FIG. 15A, that each of difference data ΔD of image data D (n, 1), D (n, 2), D (n, 3), D (n, 4), . . . , which were outputted therefrom, is distributed in relatively wide range.

The distribution is too large to assign the cause of the wide range of difference data ΔD to production variation of each of radiation detection elements 7, which is formed by laminating each layer as it was shown in FIG. 5. In addition, if it is caused by the production variation of each of radiation detection elements 7, the distribution should be a normal distribution centering ΔD=0, but, as the distribution in FIG. 15A shows, the distribution is not a normal distribution, but rather a distribution of a trapezoidal shape.

According to studies by inventors of the present patent application, it is assumed that the main cause that the distribution of each of difference data ΔD of image data outputted from each of radiation detection elements 7, which were connected with line Ln of same scanning line 5, becomes the one as it is shown in FIG. 15A, is that output characteristics of readout circuit 17, which read out image data D from each of radiation detection elements 7, vary by readout circuit 17, and therefore the output characteristic of each readout circuit 17 has variation.

Namely, in the present embodiment, as it was shown in FIG. 9, each of 2,048 readout circuits 17 formed in each of readout ICs 16 has a different output characteristic, in which a charge-voltage conversion characteristic of amplifying circuit 18, a sampling characteristic of correlated double sampling circuit 19, and the like are integrated. Due to that reason, it is assumed that, even if each of the image data, which are sent from each of radiation detection elements 17 to each of readout circuit 17, has the same value, each of image data D, which is subjected to a charge-voltage conversion at each of readout circuits 17 and is outputted, has a different value.

The difference generated in image data D by variation of the output characteristic of each of readout circuit 17 can be cleared or reduced, after transferred, for example, to an external device, by adjusting a gain correction value of each of readout circuits 17, which is multiplied to image data D (to be precise, values of image data D subtracted by offset values), at the time of image correction.

In a distribution of a trapezoidal shape as it was shown in FIG. 15A, appearance frequency F is relatively large even at difference data ΔD except for difference data ΔD at a portion of ΔD=α(α≠0) where appearance frequency F is highest and the shortest Huffman coding Hc is allotted.

Therefore, if Huffman coding Hc is allotted to each of difference data ΔD having a distribution such as shown in FIG. 15A, the number of difference data ΔD, where medium length Huffman coding Hc is allotted, becomes large. Due to the reason, it is assumed that the compression ratio of difference data ΔD becomes moderate (refer, for example to "e" of FIG. 23).

The larger the amount of radiation irradiated to radiographic-image capturing device 1, and the stronger the intensity of electromagnetic waves irradiated to each radiation detection element 7, in which the increased amount of irradiated radiation is converted into the electromagnetic waves, the larger the value itself of image data D, resulting in larger values of difference data ΔD.

Figure 15B:
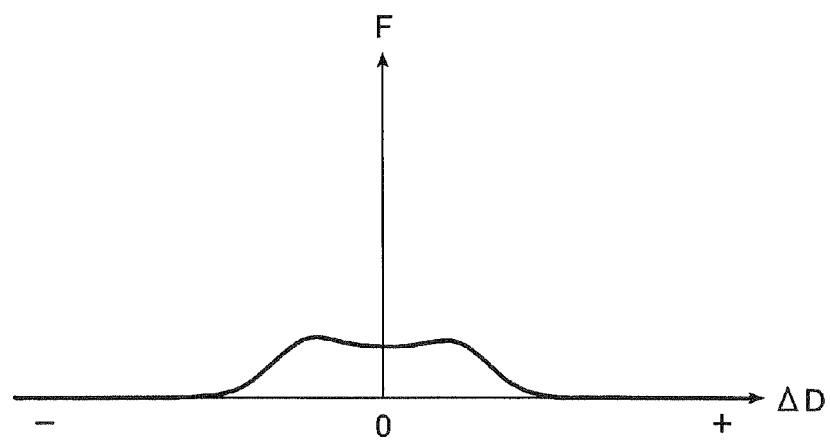
FIG. 15B is a graph showing a distribution of difference data in the case where the amount of radiation is increased in FIG. 15A.

Then, the distribution, which originally was like one of FIG. 15A, becomes one extended to both minus and plus sides, as it is shown in FIG. 15B, when the amount of radiation irradiated to radiographic-image capturing device 1 is increased. Therefore, it is assumed that the range of distribution of difference data ΔD, which are those other than difference data ΔD to which the shortest Huffman coding Hc is allotted and having relatively large appearance frequency F, extends, and then, the number of difference data ΔD to which longer Huffman coding Hc is allotted, and thereby compression ratio Rc is further worsened.

This can also be found from the fact that, for example, compared to "f" of FIG. 23, which indicates compression ratio Rc of the case where weak radiation was directly uniformly irradiated to radiographic-image capturing device 1 without an image capturing subject, compression ratio Rc of "e" of FIG. 23, which is the case where the increased amount of radiation was irradiated to radiographic-image capturing device 1 without an image capturing subject, is further worsened.

Further, it is also found that, since, in "a front chest" or "d with narrowing down" in FIG. 23, there is no or less area with no image in which radiographic-image capturing device 1 is directly irradiated by strong radiation, and only relatively weak radiation transmitted through the subject arrives at detection part P of radiographic-image capturing device 1, compression ratio Rc is relatively high, and on the other hand in the case where the area with no image is relatively large like "b front skull" or "c side of lumbar spine", compression ratio Rc is worsened.

Figure 16A:
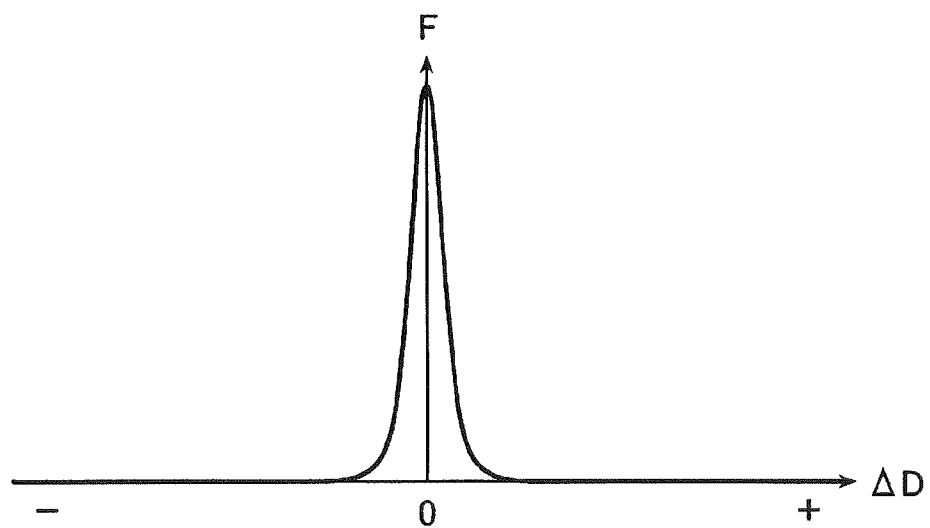
FIG. 16A is a graph showing a distribution of difference data of image data outputted from each radiation detection element connected with the same signal line when radiation is uniformly irradiated on the device.

On the other hand, if attention is focused not on each line Ln of same scanning line 5, but on each of radiation detection element (1, m), (2, m), (3, m), (4, m), . . . , connected with same signal line 6 which is disposed so as to intersect at right angles with each line Ln of same scanning line 5, in the case where the same amount of radiation is irradiated to each of above radiation detection elements 7, or electromagnetic waves having the same intensity, which were converted at scintillator 3, were irradiated, each of difference data ΔD of image data D (1, m), D (2, m), D (3, m), D (4, m), . . . , which were outputted from each of above radiation detection elements 7 shows a normal distribution centering ΔD=0, as it is shown in FIG. 16A.

As it will be found from the constitution shown in FIG. 7, image data D (1, m), D (2, m), D (3, m), D (4, m), . . . , outputted from each of radiation detection elements (1, m), (2, m), (3, m), (4, m), . . . , which were connected with same signal line 6, are subjected to charge-voltage conversion or the like by same readout circuit 17, and therefore, no influence of variation of output characteristic of each readout circuit 17 such as described above appears on a distribution of difference data ΔD. Accordingly, it is assumed that, in this case, only the influence due to production variation of each radiation detection element 7 is reflected, and thereby the distribution of difference data ΔD becomes a normal distribution as it was shown in FIG. 16A.

In the normal distribution shown in FIG. 16A, appearance frequency F of difference data ΔD at ΔD=0 to which the shortest Huffman coding Hc is allotted is significantly large, and appearance frequency F of the other difference data ΔD to which longer Huffman coding Hc is allotted becomes small. Then, when Huffman coding Hc is allotted to each of difference data ΔD having a distribution like one shown in FIG. 16A, the number of difference data ΔD, to which short Huffman coding Hc is allotted, increases, resulting in increase in compression ratio Rc of difference data ΔD.

Figure 16B:
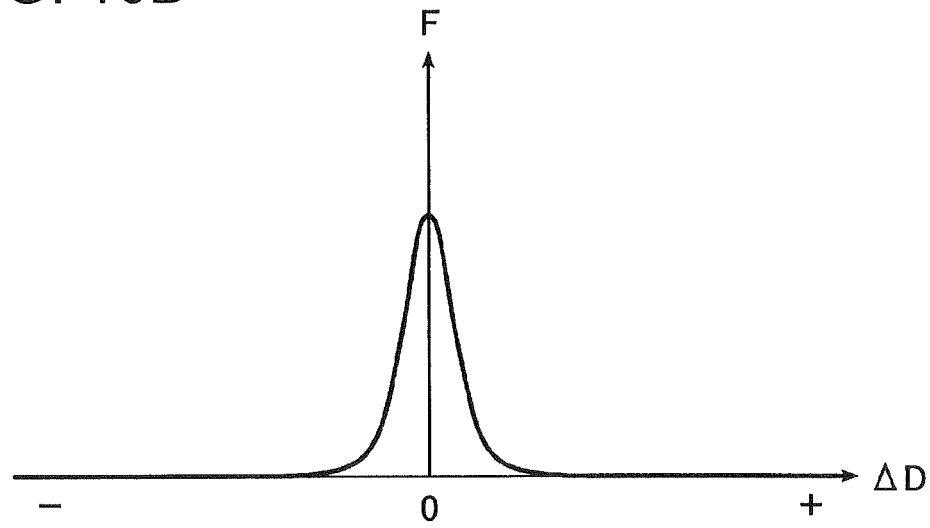
FIG. 16B is a graph showing a distribution of difference data in the case where the amount of radiation is increased in FIG. 16A.

Even if the distribution, which was originally like one shown in FIG. 16A, becomes a normal distribution in which the distribution was slightly extended to both plus and minus sides as it is shown in FIG. 16B due to a reason that, if the amount of radiation irradiated to radiographic-image capturing device 1 is increased, values of image data D themselves increase, and then values of difference data ΔD increase, after all there is no change in a fact that appearance frequency F of difference data ΔD at ΔD=0, to which the shortest Huffman coding Hc is allotted, is large, and appearance frequency F of the other difference data ΔD to which longer Huffman coding Hc is allotted becomes remarkably smaller than above appearance frequency F.

Therefore, it is assumed that when Huffman coding Hc is allotted to each of difference data ΔD having the distribution as it is shown in FIG. 16B, the number of difference data ΔD to which shorter Huffman coding Hc is allotted increases, and the compression ratio of difference data ΔD increases, and then even in the case where the amount of radiation irradiated to radiographic-image capturing device 1 is increased, compression ratio Rc of difference data ΔD is maintained in a high state.

As it was described above, the compression processing shown in FIGS. 11 to 14, in which the compression processing of image data D and difference data ΔD of the present invention, that is, the compression processing to each of image data D in the signal line direction (that is, image data D outputted from each of radiation detection elements which were connected with same signal line 6), and for difference data ΔD thereof, is the one to realize it.

Figure 17:
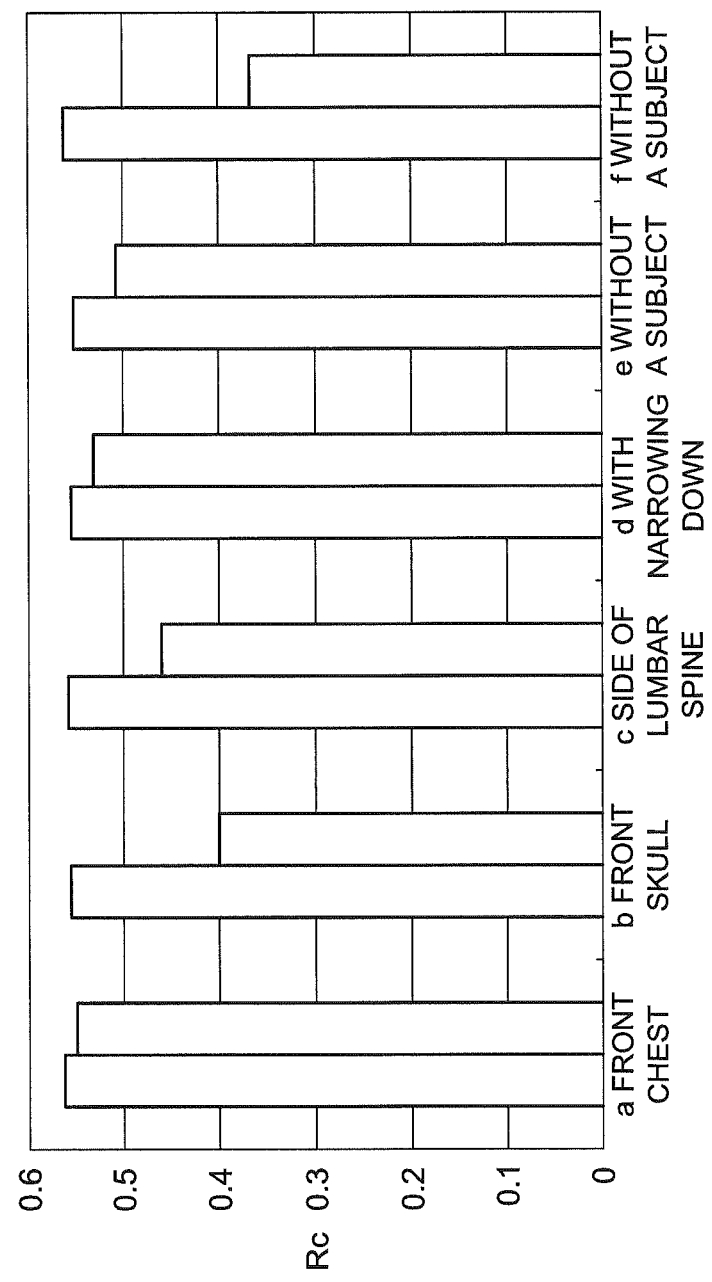
FIG. 17: Each of the left column graphs of each of "a" to "f" in FIG. 17 indicates each of compression ratios in the case where the difference data are compressed on image data of the signal line direction under each of the conditions of "a" to "f", and each of the right column graphs indicates each of compression ratios in the case where the difference data are compressed on image data which are formed in line in the scanning direction under each of the conditions of "a" to "f".

Actually, when compression processing of difference data ΔD for each of image data D in the signal direction under the totally same image capturing conditions shown in "a" to "f" of FIG. 23 is carried out, every compression ratio Rc increases compared to compression ratio Rc of each of cases of "a" to "f" of FIG. 23, as it is shown in each of left column graphs of each case of "a" to "f" of FIG. 17. The right column graphs of each case of "a" to "f" of FIG. 17 are the same ones of compression ratio Rc of each case of "a" to "f" of FIG. 23.

The results of the compression processing of image data D and difference data ΔD of the present invention, which are shown in the left column graphs of each of cases of "a" to "f" of FIG. 17 are experimental results using the same table of Huffman coding Hc which was used for the compression processing to each of conventional image data D, which form in line in the scanning direction and difference data ΔD between them, in which the results were shown in the right sides of each case.

In this way, if the compression processing of image data D and difference data ΔD in the signal line direction of the present invention is used, it becomes possible that, even if the same table of Huffman coding Hc is used, influence of variation of output characteristic of each readout circuit 17 is eliminated, and thereby compression ratio Rc in compressing each of image data D, which was obtained by radiation image capturing, and difference data ΔD between them is certainly allowed to increase.

Further, if a table of Huffman coding Hc, which is suitable for carrying out the compression processing to each of image data in the signal line direction such as one of the present invention and for difference data ΔD between them, is appropriately prepared, and then the compression processing is carried out using the above table, not the table of Huffman coding Hc used in the conventional compression processing, it becomes possible to further increase compression ratio Rc. At that time, if each table of Huffman coding Hc is appropriately prepared for each of image capturing conditions including image capturing locations of the patient, who is an image capturing subject, or the image capturing direction thereof, it is expected that each compression ratio Rc increases under each of image capturing conditions.

As it is found from the results shown in FIG. 17, characteristics of the compression processing of each of image data D and each of difference data ΔD relating to the present invention are that, as it was described above, even in each case of "a" to "f" of FIG. 17, compression ratio RC in the compression processing of each of image data D and each of difference data ΔD between them in the signal line direction relating to the present invention increases compared to that in the conventional compression processing of each of image data D and each of difference data ΔD between them, which form in line in the scanning line direction.

If we take a closer look at FIG. 17, as it is found from "a", "d", and "e" of FIG. 17, in the case where only weak radiation, which was transmitted through a subject, was irradiated to radiographic-image capturing device 1 (refer to "a" and "d" of FIG. 17), and in the case where weak radiation was irradiated to radiographic-image capturing device 1 (refer to "e" of FIG. 17), even in the conventional compression processing of each of image data D and each of difference data ΔD, the distribution range of difference data ΔD becomes relatively narrow as it was shown in FIG. 15A, and as a result, the number of difference data ΔD, to which longer Huffman coding Hc is allotted, is decreased, and thereby compression ratio Rc is increased. However, in the compression processing of each of image data D and each of difference data ΔD in the signal line direction relating to the present invention, compression ratio Rc is more increased than that of the conventional compression processing.

It is assumed that, in the compression processing of each of image data D and each of difference data ΔD in the signal line direction relating to the present invention, influence of variation of an output characteristic of each readout circuit 17 is not reflected, but, on this precise point, there is appears an effect, in which influence of only production variation of each radiation detection element 7 is reflected.

Namely, in the conventional compression processing to each of image data D and each of difference data ΔD, which form in line in the scanning line direction, in addition to the influence of production variation of each radiation detection element 7, influence of an output characteristic of each readout circuit 17 is reflected (refer to FIG. 15A), and to the contrary to that, in the compression processing of each of image data D and each of difference data ΔD in the signal line direction relating to the present invention, the compression processing is not affected by variation of the output characteristic of each readout circuit 17 as it was described above, but only influence of production variation of each radiation detection element 7 is reflected (refer to FIG. 16A).

It is assumed that, as it is evident by comparing FIG. 15A and FIG. 16A, in the compression processing of each of image data D and each of difference data ΔD relating to the present invention, the region of difference data ΔD is narrowed by the amount that the compression processing is not influenced by variation of the output characteristic of each readout circuit 17, and as a result, the number of difference data ΔD, to which longer Huffman coding Hc is allotted, is further decreased, and thereby compression ratio Rc increases.

Another characteristic of the compression processing of each of image data D and each of difference data ΔD relating to the present invention is, as it is clearly seen in the results of "e" and "f" of FIG. 17, even if the amount of radiation irradiated to radiographic-image capturing device 1 increases, compression ratio Rc is maintained in a high ratio state. Namely, in the compression processing of each of image data D and each of difference data ΔD relating to the present invention, high compression ratio Rc is maintained regardless of the amount of irradiated radiation, or independent of the amount of radiation.

The reason is assumed that, as it was shown in FIGS. 16A and 16B, even if the amount of irradiated radiation increases, and then the normal distribution of difference data ΔD a little extends to both plus and minus sides, appearance frequency F of difference data ΔD at ΔD=0, to which the shortest Huffman coding Hc is allotted, is large, and a state, in which appearance frequency F of difference data ΔD, to which the longer Huffman coding Hc than the above shortest one is allotted, becomes remarkably small, is maintained, and thereby the number of difference data ΔD, to which longer Huffman coding is allotted, does not so much increase.

In addition, an important effect accompanying the above is that, for example, as it is shown in "c" and "d" of FIG. 17, even if an area is narrowed down in the irradiation region of radiation (refer to FIG. 17d) or not (refer to FIG. 17c), at a time of image capturing of a side of the lumbar spine or the like, that is, an action is taken or not taken to eliminate or reduce a so-called area with no image where radiation is directly irradiated to the surrounding area of the lumbar spine or the like, compression ratio Rc is nearly-unchanged, and high compression ratio Rc is maintained.

In the conventional compression processing of each of image data D and each of difference data ΔD between them, which form in line in the signal line direction, as it is shown in "e" and "f" of FIG. 23 (the right column graphs of "e" and "f" of FIG. 17), the larger the amount of radiation which is directly irradiated to radiographic-image capturing device 1 without through a subject, the larger the compression ratio Rc of difference data ΔD decreased. Then, under image capturing conditions in which an area with no image of radiation is exposed at surrounding area of a subject like "front skull" of "b" and "side of lumbar spine" of "c" of FIG. 23, influence that strong radiation is directly irradiated to the area with no image, and thereby compression ratio Rc decreases reaches the entire image, resulting in decrease in compression ratio Rc of the entire image.

For this reason, as it is shown in "d" of FIG. 23, image capturing was carried out in such a way that an area with no image was eliminated or reduced by narrowing down irradiated area, and then radiation was irradiated to radiographic-image capturing device 1.

However, in the compression processing of each of image data D and each of difference data ΔD in the signal line direction relating to the present invention, as it is shown in the left column graphs of "e" and "f" of FIG. 17, high compression ratio Rc is originally maintained regardless of the amount of irradiated radiation, or independent of the amount of radiation, and therefore, even in image capturing conditions, like "b" and "c" of FIG. 17, where the area with no image is exposed in the surrounding area of a subject, compression ratio Rc is high in the area with no image, and compression ratio Rc becomes high even in area where an image of a subject was captured, resulting in high compression ratio Rc in the total image.

Therefore, there is an effect that there is no need to especially narrow down irradiated area for the purpose of increasing compression ratios Rc of image data D and difference data ΔD. In addition, there is an effect that, even in the case where image capturing is carried out without narrowing down irradiated area, it is possible to increase compression ratios Rc of image data D and difference data ΔD.

For example, in the case of image capturing of a hand of the patient as an image capturing subject, in order to prevent mistaking which hand is a right hand or a left hand of the patient which is captured in an image, there is a case where a marker such as "R" and "L" is placed at an area with no image, which image is then captured in an image together with an image capturing subject. In the case where information of an image capturing subject is taken in the area with no image, as described above, the area with no image has to be captured in the image, but if image processing for each of image data D and difference data ΔD between them in the signal line direction of the present invention is used, it becomes possible to compress image data D and difference data ΔD with high compression ratio Rc, even in the case where the area with no image is captured in the image as described above.

Even in the case where image processing for each of image data D and difference data ΔD between them in the signal line direction of the present invention is used, it is possible to narrow down an irradiated area in the area with no image to decrease the amount of image data D and difference data ΔD to be transferred, and the narrowing down the irradiated area is appropriately carried out.

As it was described above, according to radiographic-image capturing device 1 relating to the present embodiment, it was constituted in such a way that compression processing is carried out, not for the data in the conventional scanning line direction, but for each of image data D and each of difference data ΔD in the signal line direction, which is orthogonal to the above direction, that is, each of image data D and difference data ΔD between them outputted from a plurality of radiation detection elements 7 connected with the same signal lines 6, and then the compression processing is carried out for every signal line 6.

In such the constitution, since compression processing is carried out for each of image data D and difference data ΔD between them outputted from the same readout circuit 17, it becomes possible to prevent distribution of image data D and difference data ΔD from being extended depending on variation of output characteristics of each of readout circuits 17 like conventional compression processing to each of image data D and each of difference data ΔD between them, which form in line in the signal line direction, and thereby compression ratio Rc decreases. Therefore, it becomes possible to appropriately increase compression ratio Rc when image data D and each of difference data ΔD between them obtained by radiation image capturing are compressed.

Since each of image data D read out at the same readout circuit 17 and difference data ΔD between them are distributed in a form of normal distribution, a state is maintained where shorter codes are allotted to data having higher appearance frequency F, in compressed image data D and difference data ΔD (namely, Huffman cording Hc in the present embodiment), even if the amount of radiation irradiated to radiographic-image capturing device 1 increases.

Then, in radiographic-image capturing device 1 relating to the present embodiment, high compression ratio Rc can be maintained regardless of the amount of irradiated radiation. Further, for that reason, even in image capturing circumstances where an area with no image is captured in an image, it becomes possible to compress image data D and difference data ΔD with high compression ratio Rc.

Since it becomes possible to compress image data D and difference data ΔD with high compression ratio Rc like the present embodiment, the amount of data to be transferred is reduced, and transfer time is also shortened, and thereby power consumption can be decreased. In particular, as it was shown in the present embodiment, in the case where radiographic-image capturing device 1 is a battery built-in type, since power consumption of battery 41 is decreased, it becomes possible to use radiographic-image capturing device 1 for a longer time in a single charging, and thereby it becomes possible to increase efficiency in the use of radiographic-image capturing device 1.

In the present embodiment, as a table of Huffman coding Hc, all signal lines 6 are provided with a common table, and, when Huffman coding Hc is allotted to difference data ΔD, this common table is referred, but, in addition to the above, it is also possible to make a configuration so that each of signal line 6 is provided with a table of Huffman coding Hc. Further, it is also possible to make a configuration so that, for example, detection unit P is divided into a plurality of areas extending to the signal line direction, and then each of the divided areas is provided with a table of Huffman coding.

In the present embodiment, the case was described where, as it was described above, a table or a plurality of kinds of tables for each image capturing condition are stored in advance in a ROM or the like of radiographic-image capturing device 1, and control means 22 constituting a compression means carries out Huffman coding of image data D and difference data ΔD with reference to the table when compression processing is carried out, and as a result the above data are compressed.

However, it is also possible to constitute in such a way that, instead of preparing a table of Huffman coding Hc in advance, based on obtained image data D and difference data ΔD, a table of Huffman coding Hc is prepared, and then, with reference to the prepared table, Huffman coding of image data D and difference data ΔD is carried out, whereby compression processing of the data is carried out.

Specifically, control means 22 prepares, in the method, for example, shown in FIGS. 12 to 14, difference data ΔD between image data D (n, 1), D (n, 2), . . . , and image data D (n+1, 1), D (n+1, 2), . . . , of radiation detection element 7, which adjoin in the signal line direction connected with the same signal line 6, and, in doing so, each of difference data ΔD is temporarily stored in buffer memory 44c (refer to FIG. 12) without being compressed.

Then, when, the values of difference data ΔD are, for example, voted into a histogram, at a step of storing the prepared difference data ΔD in buffer memory 44c, a distribution of difference data ΔD, like one shown in FIG. 16A or 16B, is completed on the histogram at a step in which all the prepared difference data ΔD are stored in buffer memory 44c.

Control means 22 allots Huffman coding Hc to each value of difference data ΔD, based on a distribution of difference data ΔD, in such a manner that shorter Huffman coding Hc is allotted to data having higher appearance frequency F, to prepare a table of Huffman cording Hc. Then, each of difference data ΔD is read out from buffer memory 44c, and corresponding Huffman coding Hc is allotted to each of difference data ΔD, and then, each Huffman coding Hc, compressed difference data ΔD, is again stored in buffer memory 44c to be accumulated. In this case, plural buffer memories 44c used for, for example, difference data ΔD and Huffman coding Hc, may be arranged.

If configuration is made in such a manner, even if a table of Huffman coding Hc is not prepared in advance, it becomes possible to prepare a table of Huffman coding Hc based on obtained image data D or difference data ΔD, and then Huffman coding of image data D or difference data ΔD is carried out with reference to the above table, to carry out the compression processing of the data.

Also in this case, it is also possible to make a configuration so that each table of Huffman coding Hc is prepared for each signal line 6, or detection unit P is divided into a plurality of areas extending to the signal line direction, and then, for each of the divided areas, a table of Huffman coding Hc is prepared.

Also in this case, when Huffman coding Hc, that is, compressed image data D or difference data ΔD, is transferred from radiographic-image capturing device 1 to an external device, it becomes necessary to also transfer information of Huffman coding Hc, which was prepared in radiographic-image capturing device 1, to the external device. Therefore, in this case, information of the prepared table of Huffman coding Hc is subjected to reversible compression or the like, and then sent to external device, together with Huffman coding Hc.

[Radiation Image Capturing System]

Hereinafter, there will be described restoration of image data D at an external device which received compressed image data D and difference data ΔD (that is, Huffman coding Hc) transferred from radiographic-image capturing device 1 relating to the present embodiment. First, a composition of the radiographic-image capturing system will be described below.

Figure 18:
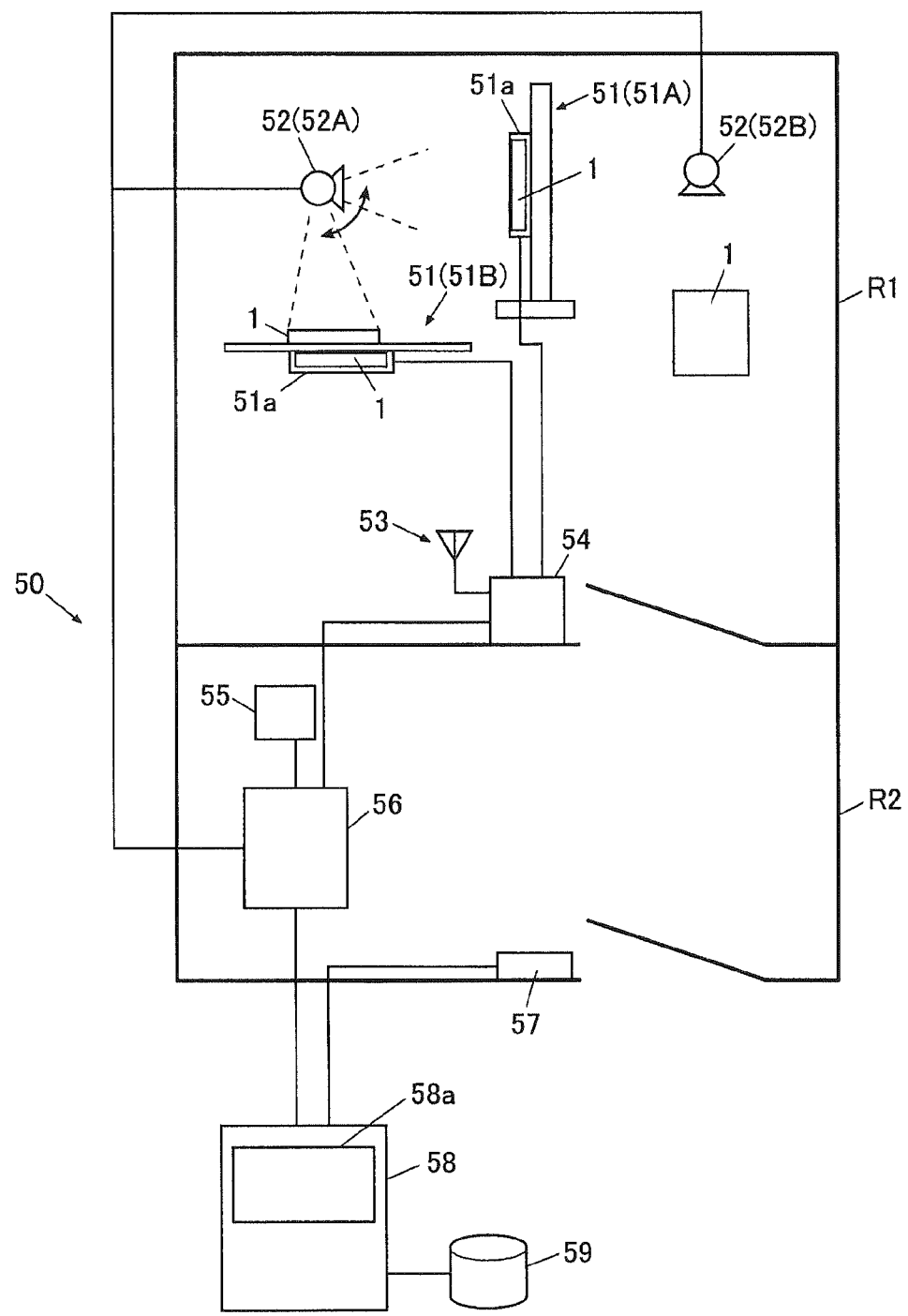
FIG. 18 is a figure showing the entire composition of radiographic-image capturing system relating to the present embodiment.

FIG. 18 is a figure showing the entire composition of radiographic-image capturing system relating to the present embodiment. Radiographic-image capturing system 50 is a system, which is assumed as radiographic-image capturing carried out in, for example, a hospital or a clinic, and the system may be adopted as the one for capturing diagnostic images for medical use as a radiographic image, but it is not necessarily limited to them.

Radiographic-image capturing system 50 is, as it is shown in FIG. 18, disposed, for example, of image capturing room R1, where image capturing of an image capturing subject (parts where images of the patient are captured), which is a part of the patient, is carried out by irradiating radiation, front room R2, where an operator such as a radiologist carries out various operations such as control of radiation irradiated to an image capturing subject, and the exterior of them.

In the present embodiment, in image capturing room R1, there are arranged Bucky device 51, which is capable of installing above-described radiographic-image capturing device 1, radiation generator 52, which is provided with a non-illustrated x-ray bulb which generates radiation irradiating to a subject, base station 54, which is provided with radio antenna 53, which, when radio communication between radiographic-image capturing device 1 and console 58 is carried out, relays the communication, and the like.

In FIG. 18, there is shown a case where portable radiographic-image capturing device 1 is used by installing it in cassette holding part 51a of Bucky device 51, but, as it was described above, radiographic-image capturing device 1 may be integrally formed with Bucky device 51, a supporting table, and the like. In addition, as it is shown in FIG. 18, it is possible to configure so that radiographic-image capturing device 1 is cable connected with base station 54, and then, through the cable, data can be sent with cable communication.

In front room R2, there are arranged operation table 56, which controls irradiation of radiation, and is provided with switching means 55 to indicate a start of irradiation of radiation to radiation generator 52, and tag reader 57, which detects a tag, which will be described later, incorporated in radiographic-image capturing device 1.

In the present embodiment, console 58, which controls the entire radiographic-image capturing system 50, is arranged at the outside of image capturing room R1 and front room R2, but it is possible to configure so that, for example, console 58 is arranged in front room R2. Further, memorizing means 59, which is composed of a hard disk and the like, is connected with console 58.

The configuration of radiographic-image capturing device 1 is as described above, but in the present embodiment, radiographic-image capturing device 1 further has a following configuration. However, the following configuration is not an essential one.

Specifically, in radiographic-image capturing device 1, a non-illustrated tag is incorporated. In the present embodiment, a tag a so-called RFID (radio frequency identification)

tag is used, and in the tag, there are compactly incorporated a control circuit for controlling each part of the tag and a memorizing part for memorizing inherent information of radiographic-image capturing device 1. The inherent information includes, for example, cassette ID, information on a type of scintillator, size information, resolution, and the like, as identification information allotted to radiographic-image capturing device 1.

Radiographic-image capturing device 1 is, as it is described above, sometimes installed in Bucky device 51, but it may also be used as single device without being installed in Bucky device 51.

Namely, it is designed in such a manner that radiographic-image capturing device 1 can be used, in single state, for example, by arranging it on the upper side of a bed placed in image capturing room R1, Bucky device 51B used for image capturing in supine position, as it is shown in FIG. 18, or the like, and then placing a hand or the like of the patient, who is a image capturing subject, on radiation entering surface R (refer to FIG. 1) thereof, or by, for example, inserting it between a bed and the lower back or the foot of the patient who lies on a bed. In this case, radiographic-image capturing is carried out by, for example, irradiating radiation to radiographic-image capturing device 1 through the subject from portable radiation generator 52B, or the like.

Console 58 is configured of a computer, in which non-illustrated CPU, ROM, RAM, input-output interface and the like are connected with a bus, and the like. Predetermined programs are stored in the ROM, and console 58 reads out a necessary program, develops it in the work area of RAM, and, according to the program, executes various processing and then, as it was described above, controls total radiographic-image capturing system 50.

With console 58, there are connected above-described operation table 56, tag reader 57, memorizing means 59, and the like, and further, Bucky devices 51A and 51B used for image capturing in upright and supine positions, and the like through base station 54 or operation table 56. In addition, in console 58, there is arranged display screen 58a comprising a CRT (cathode ray tube), an LCD (liquid crystal display) and the like, and, in addition to them, with console 58, there are connected non-illustrated input means such as a keyboard and a mouse.

Hereinafter, there will be described restoration processing of image data D in console 58, as well as an action of radiographic-image capturing system 50 relating to the present embodiment.

Console 58 is designed in such a manner that, when console 58 of Huffman coding Hc, that is, compressed image data D or difference data ΔD, is transferred from radiographic-image capturing device 1 through antenna device 39 or a cable, via base station 54, or the like, the transferred data are temporarily stored in memorizing means 59, after which image data D are restored based on them.

First, there will be described a case where console 58 is already provided with a common table of Huffman coding Hc with radiographic-image capturing device 1. In this case, the table of Huffman coding is already stored in a ROM or memorizing means 59 in console 58, and console 58 reads out the table from it and carries out restoration.

As it was described above, in the case where, at radiographic-image capturing device 1, without preparing difference data ΔD of each of image data D, each of image data D is subjected to a compression processing using a table of Huffman coding, Huffman coding Hc, compressed image data D, is transferred from radiographic-image capturing device 1. In this case, console 58, with reference to the read out table of Huffman coding Hc, decompresses each Huffman coding to restore the original above image data.

Further, in the case where Huffman coding Hc, compressed difference data ΔD, is transferred from radiographic-image capturing device 1, console 58, with reference to the read out table of Huffman coding Hc, decompresses each Huffman coding into original difference data ΔD to restore original image data D, based on decompressed original difference data ΔD.

In this case, also in console 58 side, above-described reference data Dc (1), Dc (2), Dc (3), Dc (4), . . . are already stored in a ROM, memorizing means 59, or the like, and therefore console 58 first reads out these reference data Dc (1), Dc (2), Dc (3), Dc (4), . . . .

Then, with reference to a table of Huffman coding Hc, console 58 decomposes Huffman coding Hc, which corresponds each of difference data ΔD (1, 1), ΔD (1, 2), ΔD (1, 3), ΔD (1, 4), . . . , to restore original difference data ΔD (1, 1), ΔD (1, 2), ΔD (1, 3), ΔD (1, 4), . . . , and then calculates Formula (1), to restore original image data D (1, 1), D (1, 2), D (1, 3), D (1, 4), . . . , which form in line in the scanning line direction.

$$Dc(m)+\Delta D(1,m) \rightarrow D(1,m) \qquad \text{Formula (1):}$$

This processing corresponds to reverse processing for each of image data D (1, 1), D (1, 2), D (1, 3), D (1, 4), . . . , which were read out from each radiation detection element 7 connected with line L1 of scanning line 5, which was shown in FIG. 13, and form in line in the scanning direction.

Console 58 stores restored image data D (1, 1), D (1, 2), D (1, 3), D (1, 4), . . . , in memorizing means 59.

Further, console 58, with reference to a table of Huffman coding Hc, decomposes Huffman coding Hc, which corresponds to each of difference data ΔD (2, 1), ΔD (2, 2), ΔD (2, 3), ΔD (2, 4), . . . , to restore original difference data ΔD (2, 1), ΔD (2, 2), ΔD (2, 3), ΔD (2, 4), . . . .

Then, using previously restored image data D (1, 1), D (1, 2), D (1, 3), D (1, 4), . . . , calculation is carried out using Formula (2) to restore original image data D (2, 1), D (2, 2), D (2, 3), D (2, 4), . . . , which form in line in the scanning line direction, and then restored image data D (2, 1), D (2, 2), D (2, 3), D (2, 4), . . . , are stored in memorizing means 59.

$$D(1,m)+\Delta D(2,m) \rightarrow D(2,m) \qquad \text{Formula (2):}$$

In this way, console 58, with reference to a table of Huffman coding Hc, decompresses Huffman coding Hc corresponding to each of difference data ΔD (n, m), to restore original difference data ΔD (n, m), and then calculation is carried out using Formula (3), using previously calculated image data D (n−1, m), and thereby all image data D (n, m) are successively restored.

$$D(n-1,m)+\Delta D(n,m) \rightarrow D(n,m) \qquad \text{Formula (3):}$$

As it was described above, in the case where it is constituted so that information of the number of the used table, or the like is transferred from radiographic-image capturing device 1 to console 58, in the case where radiographic-image capturing device 1 and console 58 are commonly provided with a plurality kinds of tables of Huffman coding, console 58 is constituted so that it reads out a table specified by information on the transferred number, or the like from a ROM, memorizing means 59, or the like, and then, using the table, performs decompression or restoration processing.

In the radiographic-image capturing system 50 such as described above, before image capturing, in console 58, above described order information of image capturing which specifies image capturing locations of the patient, who is an image capturing subject, or the image capturing direction, is often prepared. Therefore, it is also possible to constitute in such a manner that, when image capturing is carried out based on the above order information of image capturing, image capturing conditions including image capturing locations and the image capturing direction are specified, in radiographic-image capturing device 1 side, based on the order information of image capturing, and then a table of Huffman coding Hc corresponding to above image capturing conditions is selected, and thereby, also in console 58 side, without receiving translation of information of the number of the used table or the like from radiographic-image capturing device 1, a table of Huffman coding Hc to be used is selected based on order information of image capturing itself.

Further, it is also possible, as it was described above, to constitute in such a manner that, in the case of making a constitution so that a table of Huffman coding Hc, which is appropriate to the image capturing condition of the aforesaid radiographic-image capturing is transferred, at every radiographic-image capturing, from console 58 side, which is an external device, to radiographic-image capturing device 1, when image data D or difference data ΔD, which was compressed with reference to the aforesaid table, are transferred from radiographic-image capturing device 1, decompression or restoration is carried out at console 58 side with reference to the same table of Huffman coding Hc as the one which was transferred to radiographic-image capturing device 1.

On the other hand, as it was described above, it is also possible to constitute so that, at every time compression processing of image data D or difference data ΔD is carried out in radiographic-image capturing device 1, a table of Huffman coding Hc is prepared. In this case, console 58 restores image data D by, for example, restoring original difference data ΔD in the similar way to the above with reference to a table of Huffman coding Hc transferred from radiographic-image capturing device 1 together with Huffman coding Hc.

In this case, it may be constituted so that the above reference data Dc (1), Dc (2), Dc (3), Dc (4), . . . are also prepared at every time image data D or difference data ΔD is carried out in radiographic-image capturing device 1. In that case, it is constituted in such a manner that console 58 restores image data D by, for example, restoring original difference data ΔD in the similar way to the above based on reference data Dc transferred together with Huffman coding Hc.

As it was described above, according to radiographic-image capturing system 50 relating to the present embodiment, it becomes possible to restore compressed image data D or difference data ΔD transferred from radiographic-image capturing device 1 so as to fully agree with original image data D or original difference data ΔD, and thereby it becomes possible to certainly restore each of image data D captured by radiographic-image capturing device 1.

Further, also in radiographic-image capturing system 50 relating to the present embodiment, since compression processing is carried out for each of image data D or each of difference data ΔD in the signal line direction in radiographic-image capturing device 1, it becomes possible to compress image data D or difference data ΔD with high compression ratio Rc, and thereby effects, such as a shorter transmission time of data, and reduced power consumption are obtained. Therefore, as the total system, it becomes possible to shorten data transmission time and to reduce power consumption.

[In the Case of Thinned-Out Data]

There may be a constitution in such a manner that, before displaying the entire image data D of radiation images, which were captured by radiographic-image capturing device 1, on display screen 58a of console 58 of radiographic-image capturing system, images in which pixels were thinned out at a predetermined ratio from image data D, so-called thinned-out images, are displayed for preview use.

In this case, radiographic-image capturing device 1 transfers the thinned-out image data (hereinafter it is referred to as thinned-out data) to console 58, after which automatically transfers the remaining image data or the entire image data D to console 58.

Further, there may be a constitution in such a manner that an operator such as a radiologist observes the thinned-out images for preview use, and then determines whether or not a subject is appropriately captured in images (in thinned-out images) captured by radiographic-image capturing device 1. In this case, if the operator observes the thinned-out images, and confirms that a subject is appropriately captured in the images, the operator transfers again the entire image data or the like from radiographic-image capturing device 1, and if the operator finds that a subject is not appropriately captured in the images, the operator allows radiographic-image capturing device 1 to throw the aforesaid image data away, and again carries out works such as radiographic-image capturing.

As a method for preparing thinned-out data by control means 22 as a thinned-out data generating means at radiographic-image capturing device 1, various methods may be adopted. But first of all, there will be described a case of preparing thinned-out data in a way of extracting each of image data D, which form in line in the scanning line direction, at every predetermined number of lines, among each of image data D outputted from each of radiation detecting element 7 connected with each of line L1 to Lx of scanning line 5.

In FIG. 19 and FIGS. 20 to 22, which will be described later, similarly to FIGS. 9 to 11, the horizontal direction is the scanning line direction, and the vertical direction is the signal line direction. In the case of FIG. 19, there is described a case in which each of image data D, outputted from each of radiation detecting element 7 connected to shaded lines L1, L4, L7, . . . at every two lines of scanning line 5, is prepared as thinned-out data, but it is possible to set the above predetermined number of lines for thinning out image data D to an appropriate number of lines, and it is not limited to the case at every two lines.

In this case, control means 22 of radiographic-image capturing device 1 prepares difference data ΔD of image data D in the signal line direction by the similar processing to the one shown in FIGS. 12 to 14 or in others, and at that time, control means 22 reads out only image data, which forms in line in the direction of lines L1, L2, L3, L4, . . . of scanning line 5 from memorizing means 40 of radiographic-image capturing device 1.

Namely, control means 22 first reads out, from memorizing means 40, image data D (1, 1), D (1, 2), D (1, 3), D (1, 4), . . . , which form in line in the line L1 direction of scanning line 5, prepares difference data ΔD (1, 1), ΔD (1, 2), ΔD (1, 3), ΔD (1, 4), . . . , between reference data Dc (1), Dc (2), Dc (3), Dc (4), . . . , and image data thereof, and compresses difference data ΔD thereof with reference to a table of Huffman coding Hc.

Next, control means 22, after omitting each of image data D, which form in line in the direction of lines L2 and L3 of scanning line 5, reads out, from memorizing means 40, image data D (4, 1), D (4, 2), D (4, 3), D (4, 4), . . . , which form in line in the line L4 direction of scanning line 5, prepares difference data ΔD (4, 1), ΔD (4, 2), ΔD (4, 3), ΔD (4, 4), . . . , between image data D (1, 1), D (1, 2), D (1, 3), D (1, 4), . . . , which form in line in the line L1 direction of scanning line 5 and image data thereof, and compresses difference data ΔD thereof with reference to a table of Huffman coding Hc.

In this way, in the following, the similar processing, in which difference data ΔD for each of image data D forming in line at lines L7, L10, . . . , are prepared and compressed, is repeated. The above processing is equivalent to one in which, as it is shown in FIG. 19B, image data D forming inline in the direction of lines L1, L4, L7, . . . of scanning line 5 are extracted as thinned out data, and the extracted data are compressed in the similar manner to the above embodiment.

It is the same as described above that it is possible to make a constitution in such a manner that, without preparing difference data ΔD of each of image data D, each of image data D, which were read out from memorizing means 40 and form in line in the direction of L1, L4, L7, . . . of scanning line 5, is compressed without any changes.

On the other hand, in the case where Huffman coding Hc, compressed image data D, is transferred from radiographic-image capturing device 1, console 58 decompresses each Huffman coding Hc to restore the original image data, with reference to a table of Huffman coding Hc read out from a ROM or the like.

Further, as it was described above, in the case where Huffman coding Hc, compressed difference data ΔD, is transferred from radiographic-image capturing device 1, console 58, in the similar manner to the above, decompresses each Huffman coding Hc into original difference data ΔD with reference to a table of read out Huffman coding Hc, and restores original image data D based on decompressed difference data ΔD, by using reference data Dc (1), Dc (2), Dc (3), Dc (4), . . . , or the like.

Then, console 58 forms thinned-out images based on restored original image data D, and displays them on display screen 58a (refer to FIG. 18). At that time, it may be constituted so that the thinned-out data are displayed on display screen 58a, after the entire data of the thinned-out images are prepared, and it is also possible to constitute so that, at every time when each of image data D forming in line in the direction of L1, L4, L7, . . . of scanning line 5 is restored, the restored data are successively displayed on display screen 58a.

As it was described above, in the case where it is constituted so that entire image data D (or entire difference data ΔD) are transferred after an operator confirms the thinned-out data, console 58 waits an input of instruction from the operator. In the case where an operator observed thinned-out images displayed on display screen 58a, and determined that an image of subject was appropriately captured in images, the operator, through console 58, or the like, allows radiographic-image capturing device 1 to throw away unnecessary image data D obtained at the aforesaid radiographic-image capturing, and carries out again image capturing, and in the case where the operator determined that an image of subject was appropriately captured, the operator, through console 58, transmits a request signal to transfer other image data D obtained by the aforesaid radiographic-image capturing to radiographic-image capturing device 1.

When control means 22 of radiographic-image capturing device 1 receives a transfer request of other image data D from console 58, control means 22 next starts reading out, from memorizing means 40, only each of image data, which form in line in the direction of remaining lines L2, L3, L5, L6, . . . , of scanning line 5. As it was described above, in the case where it is constituted so that, after thinned-out data were transferred, the entire image data D (or difference data ΔD) are automatically transferred, only above each of image data D is automatically read out without waiting the transfer request from console 58.

Namely, control means 22 first reads out, from memorizing means 40, image data D (2, 1), D (2 2), D (2, 3), D (2, 4), . . . , which form in line in the line L2 direction of scanning line 5, prepares difference data ΔD (2, 1), ΔD (2, 2), ΔD (2, 3), ΔD (2, 4), . . . , between reference data Dc (1), Dc (2), Dc (3), Dc (4), . . . , and image data thereof, and compresses difference data ΔD thereof with reference to a table of Huffman coding Hc.

Next, control means 22 reads out, from memorizing means 40, image data D (3, 1), D (3, 2), D (3, 3), D (3, 4), . . . , which form in line in the line L2 direction of scanning line 5, prepares difference data ΔD (3, 1), ΔD (3, 2), ΔD (3, 3), ΔD (3, 4), . . . , between image data D (2, 1), D (2, 2), D (2, 3), D (2, 4), . . . , which form in line in the line L2 direction of scanning line 5 and image data thereof, and compresses difference data ΔD thereof with reference to a table of Huffman coding Hc.

In this way, in the following, the similar processing, in which difference data ΔD for each of image data D forming in line at lines L5, L6, L8, . . . , are prepared and compressed, is repeated. The above processing is equivalent to one in which, as it is shown in FIG. 20, image data D forming inline in the direction of lines L2, L3, L5, L6, . . . of scanning line 5 are extracted, and the extracted data are compressed in the similar manner to the above embodiment.

In the case where Huffman coding Hc, remaining compressed image data D, is transferred from radiographic-image capturing device 1, console 58 decompresses each Huffman coding Hc to restore the original image data, with reference to a table of Huffman coding Hc read out from a ROM or the like.

Further, as it was described above, in the case where Huffman coding Hc, compressed difference data ΔD, is transferred from radiographic-image capturing device 1, console 58, in the similar manner to the above, decompresses each Huffman coding Hc into original difference data ΔD with reference to a table of read out Huffman coding Hc, and restores original image data D based on decompressed difference data ΔD, by using reference data Dc (1), Dc (2), Dc (3), Dc (4), . . . , or the like.

Then, console 58 combines restored original remaining image data D and image data D, which were previously transferred as thinned-out images and restored to make a whole one, and thereby restores original entire image data D, which is shown in FIG. 19A. Then, based on the data, complete radiographic images, not thinned-out images, are formed.

Console 58 stores restored original entire image data D in memorizing means 59, and at the same time, console 58, according to instructions of an operator, or automatically, carries out image correction processing such as the above-described gain correction, for restored original entire image data D or displays them on display screen 58a. Also in this case, it may be constituted so that, original entire image data D are restored, after which the restored data are displayed on display screen 58a, and it is also possible to constitute so that, at every time when each of image data D forming in line in the direction of L1 to Lx of scanning line 5 is restored, the restored data are successively displayed on display screen 58a.

In the above embodiment, it was described the case where image data D, which form inline in the direction of lines L1, L4, L7, . . . of scanning line 5, and are equivalent to thinned-out data, and each of remaining image data D, which form inline in the direction of lines L2, L3, L5, L6, . . . of scanning line 5, are independently subjected to Huffman encoding, and then are independently restored. However, other than that, it is also possible to constitute, in such a manner that, for example, each of image data D, which form in line in the direction of remaining lines L2, L3, L5, L6, . . . of scanning line 5, is subjected to Huffman encoding by making them dependent on image data D, which form in line in the direction of lines L1, L4, L7, . . . of scanning line 5, and are equivalent to thinned-out data, to restore them.

Specifically, for each of data D, which form in line in the T 7 direction of scanning line 5, instead of preparing, as it is described above, difference data ΔD between reference data Dc (1), Dc (2), Dc (3), Dc (4), . . . , and image data D thereof, difference data ΔD (2, 1), ΔD (2, 2), ΔD (2, 3), ΔD (2, 4), . . . between each of image data D (1, 1), D (1, 2), D (1, 3), D (1, 4), . . . , which form in line in the L1 direction of scanning line 5, and each of image data D (2, 1), D (2, 2), D (2, 3), D (2, 4), . . . , which form in line in the L2 direction of scanning line 5, are prepared, as it is shown FIG. 21, and then above difference data ΔD are compressed with reference to a table of Huffman coding Hc.

For each of data D, which form in line in the L3 direction of scanning line 5, difference data ΔD (3, 1), ΔD (3, 2), ΔD (3, 3), ΔD (3, 4), . . . between the above each of data D and each of image data D (2, 1), D (2, 2), D (2, 3), D (2, 4), . . . , which form in line in the L2 direction of scanning line 5, are prepared, and then above difference data ΔD are compressed with reference to a table of Huffman coding Hc.

For each of data D, which form in line in the direction of lines L5, L8, L11, . . . of scanning line 5, difference data ΔD between the above each of data D and each of image data D, which form in line in the direction of lines L4, L7, L10, . . . of scanning line 5, are prepared; and, for each of data D, which form in line in the direction of lines L6, L9, L12, . . . of scanning line 5, difference data ΔD between the above each of data D and each of image data D, which form in line in the direction of lines L5, L8, L11, . . . of scanning line 5, are prepared, and then, each of difference data ΔD thereof is compressed.

Console 58 decompresses, with reference a table of Huffman coding Hc, each Huffman coding Hc, compressed each of difference data ΔD, into original difference data ΔD. Then, each of image data D, which form in line in the direction of lines L1, L4, L7, L10, . . . of scanning line 5, which are already restored as thinned-out data, and difference data ΔD (2, 1), . . . , ΔD (5, 1), . . . , ΔD (8, 1), . . . , ΔD (11, 1), . . . , which were decompressed and restored, are added to restore original each image data D, which form in line in the direction of lines L2, L5, L8, L11, . . . of scanning line 5.

Further, each of restored original image data D, which form in line in the direction of lines L2, L5, L8, L11, . . . of scanning line 5, and difference data ΔD (3, 1), . . . , ΔD (6, 1), . . . , ΔD (9, 1), . . . , ΔD (12, 1), . . . , which were decompressed and restored, are added to restore original each image data D, which form in line in the direction of lines L3, L6, L9, L12, . . . of scanning line 5.

It is also possible to constitute in such a manner that, in this way, remaining original image data D are restored, and the restored data are combined with image data D, which were previously transferred and restored, to make a whole one, and thereby original entire image data D, which is shown in FIG. 19A are restored to form complete radiographic images.

Further, there is also a case where, as a way to prepare thinned-out data in radiographic-image capturing device 1, the thinned-out data are prepared in such a manner that, by extracting image data D, for example, in the scanning line direction and in the signal line direction, at every predetermined number of radiation detection element 7, the amount of data are reduced to ⅑, 1/16, or the like of the total image data D.

In such the case, control means 22 repeats processing that control means 22 reads out image data D (1, 1), D (1, 4), . . . from memorizing means 40, and prepares difference data ΔD (1, 1), ΔD (1, 4), . . . between the above data and reference data Dc (1), Dc (4), . . . , and subsequently, reads out image data D (4, 1), D (4, 4), . . . from memorizing means 40, and prepares difference data ΔD (4, 1), ΔD (4, 4), . . . between the above data and image data D (1, 1), D (1, 4), . . . , and prepares each of difference data ΔD. Then, in the similar manner as above, difference data ΔD are compressed with reference to a table of Huffman coding Hc, which compressed data are then transferred to console 58.

Console 58, in the similar manner to the above, decompresses Huffman coding Hc, compressed difference data ΔD transferred from radiographic-image capturing device 1, into original difference data ΔD with reference to a table of Huffman coding Hc, and then restores original image data D based on decompressed original difference data ΔD, by using reference data Dc (1), Dc (4), . . . , or the like.

When control means 22 of radiographic-image capturing device 1 receives a transfer request of other image data D from console 58, or after thinned-out data are transferred, control means 22 automatically prepares difference data ΔD, in the similar way as described above, for remaining image data D, compresses and transfers them.

Namely, for image data D, each of which forms in line in downward from each of D (1, 1), D (1, 4), . . . (that is, forms in line in the signal line) in FIG. 22, each of difference data ΔD is prepared in the similar way of the above case of line thinning out (that is, in the way shown in FIG. 20 or FIG. 21), and for image data D, each of which forms in line in downward from each of D (1, 2), D (1, 3), D (1, 5), D (1, 6), . . . , each of difference data ΔD is prepared in a way of preparing difference data ΔD for general image data D (refer to FIGS. 11 to 14), and then compressed.

In console 58, for image data D, each of which forms in line in downward from each of D (1, 1), D (1, 4), . . . in FIG. 22, Huffman coding Hc, compressed difference data ΔD, is decomposed into original difference data ΔD in the similar way of the above case, and then original image data D are restored based on them. For image data D, each of which forms in line in downward from each of D (1, 2), D (1, 3), D (1, 5), D (1,6), . . . , Huffman coding Hc, compressed difference data ΔD, is decompressed into original difference data ΔD in a way of decompression and restoration of difference data ΔD for general image data D, and then original image data D are restored based on them.

Then, restored original remaining image data D and image data D, which were previously transferred as thinned-out images and restored are combined to make a whole one, and thereby original entire image data D shown in FIG. 22 are completely restored.

In this case, since the processing for image data D, each of which forms in line in downward from each of D (1, 1), D (1, 4), . . . (that is, forms in line in the signal line) in FIG. 22, becomes different from the processing for image data D, each of which forms in line in downward from each of D (1, 2), D (1, 3), D (1, 5), D (1, 6), . . . , the constitution of preparation or compression of difference data ΔD, or of decompression or restoration at console 58 side may become complicated.

For that reason, in the case of adopting a way of preparing thinned-out data as it is shown in FIG. 22, when preparing and compressing entire image data D or difference data ΔD which are transferred after thinned-out image being transferred, instead of restoring remaining image data D by using, as it was shown in FIG. 20 or FIG. 21, thinned-out image which were already transferred to console 58 side, a constitution, in which, using a way shown in FIGS. 11 to 14, or the like, regular processing for entire image data is again carried out, may become simple in constitution of each processing.

In this way, a way of preparation or compression of entire image data D or difference data ΔD which are transferred after thinned-out image being transferred is appropriately determined in consideration of an interface or the like between radiographic-image capturing device 1 and console 58.

There is also a case where it takes not so much time for data transfer, when transferring the thinned-out data, even if uncompressed data, so-called raw thinned-out data, are transferred to console 58 without any processing, without compressing the thinned-out data, or preparing and compressing difference data ΔD thereof. Namely, there is also a case where time difference of transfer to be completed between a case where difference data ΔD are prepared from thinned-out data and then compressed to be transferred, and a case where raw thinned-out data, which are not compressed, are transferred, is small.

In such the case, it is also possible to constitute so that an operator selects a case where thinned-out data are transferred without any changes or a case where difference data ΔD are prepared from thinned-out data and then compressed to be transferred.

As it was described above, according to radiographic-image capturing device 1 and radiographic-image capturing system relating to the present embodiment, even in the case where data of thinned-out images are compressed, and then transferred, if the similar compression is carried out to one for general image data D or difference data ΔD, which was shown in the above embodiment, it becomes possible to compress data of thinned-out images with high compression ratio Rc, and thereby it becomes possible to shorten data transfer time, resulting in reduced electric power consumption.

There was described a case where the above compression processing at radiographic-image capturing device 1 and decompression processing at console 58 of the above data of thinned-out images were carried out with reference to a table of Huffman coding Hc, which was read out from control means 22 of radiographic-image capturing device 1, a ROM of console 58, or the like. However, it is obvious that it is possible to constitute in such a manner that, even in the compression or decompression processing of data of thinned-out images, a table is used by selecting it from a plurality of provided tables, a table prepared at radiographic-image capturing device 1 is transferred to console 58, or a table is transmitted from console 58 to radiographic-image capturing device 1 at every radiographic-image capturing.

The invention claimed is:

1. A radiographic-image capturing device comprising:
a detecting unit provided with a plurality of scanning lines and a plurality of signal lines arranged so as to intersect with each other, and a plurality of radiation detection elements arranged two-dimensionally each of which is arranged at each of areas partitioned by the plurality of scanning lines and the plurality of signal lines;
a read-out circuit which reads out electric charges from the radiation detection elements via the signal lines, converts the electric charge to an electric signal for each of the radiation detection elements, and outputs the electric signal as image data; and
a compression section which performs compression processing to image data for each of the radiation detection elements,
wherein the compression section performs compression processing to each of image data outputted from a plurality of radiation detection elements connected with a same signal line for each of the signal lines.

2. The radiographic-image capturing device described in claim 1, provided with a table of Huffman codes for the compression processing in advance,
wherein the compression section performs a compression processing to the image data or the difference data for each of the radiation detecting elements, by performing Huffman coding of the image data and the difference data referring the table.

3. The radiographic-image capturing device described in claim 1, provided with a table of Huffman codes for the compression processing for each of radiographing conditions including a radiographing position of body of a patient who is a radiographing target, in advance,
wherein the compression section selects the table corresponding to specified radiographing condition and performs compression processing to the image data or the difference data for each of the radiation detecting elements, by performing Huffman coding of the image data or the difference data referring the selected table.

4. The radiographic-image capturing device described in claim 1,
wherein the compression section generates a table of Huffman codes for compression processing based on the image data and the difference data when performing the compression processing to the image data and the difference data, and performs compression processing to the image data for each of the radiation detecting elements, by performing Huffman coding of the image data or the difference data referring the table.

5. The radiographic-image capturing device described in claim 1,
wherein the compression section performs compression processing to the image data or the difference data for each of the radiation detecting elements, by performing Huffman coding of the image data or the difference data referring a table of Huffman codes for the compression processing, the table incoming for each of radiographings.

6. A radiographic-image capturing system comprising:
the radiographic-image capturing device described in claim 5 provided with a transfer section transferring the image data subjected to the compression processing or the difference data subjected to the compression processing; and
a console which transmits the table of Huffman codes for the compression processing for each of radiographings,
wherein the console decompresses the difference data subjected to the compression processing transferred from the radiographic-image capturing device into the original difference data, by referring the table of Huffman codes incoming from the radiographic-image capturing device, and restores the original image data based on the decompressed original difference data.

7. A radiographic-image capturing system comprising:
the radiographic-image capturing device described in claim 1 provided with a transfer section transferring the image data subjected to the compression processing; and a console for decompressing the image data subjected to the compression processing transferred from the radiographic-image capturing device, and restoring the original image data.

8. A radiographic-image capturing device comprising:
a detecting unit provided with a plurality of scanning lines and a plurality of signal lines arranged so as to intersect with each other, and a plurality of radiation detection elements arranged two-dimensionally each of which is arranged at each of areas partitioned by the plurality of scanning lines and the plurality of signal lines;
a read-out circuit which reads out electric charges from the radiation detection elements via the signal lines, converts the electric charge to an electric signal for each of the radiation detection elements, and outputs the electric signal as image data; and
a compression section which performs compression processing to image data for each of the radiation detection elements,
wherein the compression section prepares difference data by calculating difference between image data of the radiation detection elements adjoining to each other for each of the image data outputted from a plurality of radiation detection elements connected to a same signal line, and performs compression processing to the difference data.

9. The radiographic-image capturing device described in claim 8,
comprising at least two buffer registers each of which temporarily accumulates each of the image data aligning in a direction of the scanning line outputted from each of the radiation detection elements by setting a switching section to ON state via the scanning line, or each of the image data aligning in the direction of the scanning line read out from a memory,
wherein the compression section prepares the difference data between the image data of the adjoining radiation detection elements connected to the same signal line, by temporarily accumulating each of the image data aligning in the direction of the scanning line of adjoining scanning lines in the two buffer registers and calculating a difference between image data each other of same addresses of the two buffer registers.

10. The radiographic-image capturing device described in claim 9,
wherein, after calculating the difference between the image data each other aligning in the direction of the scanning line of adjoining scanning lines, the compression section transfers image data aligning in the direction of the scanning line of one of the adjoining scanning lines from a currently accumulated buffer register to the other register buffer, accumulates each of the image data aligning in the direction of the scanning line of a scanning line adjoining the one scanning line to the emptied buffer register, and prepares the difference data by repeating the processing of calculating the difference between the image data each other of same addresses of the two buffer registers.

11. The radiographic-image capturing device described in claim 9,
wherein the compression section is provided with reference data which represents a reference when calculating difference of each of the image data each other aligning in the direction of the scanning line of a first scanning line.

12. The radiographic-image capturing device described in claim 8,
comprising at least one buffer register which temporarily accumulates each of the image data aligning in a direction of the scanning line outputted from each of the radiation detection elements by setting a switching section to ON state via the scanning line, or each of the image data aligning in the direction of the scanning line read out from a memory,
wherein the compression section prepares the difference data between image data each other of the adjoining radiation detection elements connected to the same signal line, by temporarily accumulating in the one buffer register each of the image data aligning in the direction of the scanning line of one of the adjoining scanning lines and calculating the difference between the image data each other when accumulating each of the image data aligning in the direction of the scanning line of an other scanning line while replacing each of the image data corresponding each of the image data of the one scanning line.

13. A radiographic-image capturing system comprising:
the radiographic-image capturing device described in claim 8 provided with a transfer section transferring the difference data subjected to the compression processing; and
a console for decompressing the difference data subjected to the compression processing transferred from the radiographic-image capturing device, and restoring the original image data based on the decompressed difference data which is the original difference data.

14. A radiographic-image capturing device comprising:
a detecting unit provided with a plurality of scanning lines and a plurality of signal lines arranged so as to intersect with each other, and a plurality of radiation detection elements arranged two-dimensionally each of which is arranged at each of areas partitioned by the plurality of scanning lines and the plurality of signal lines;
a read-out circuit which reads out electric charges from the radiation detection elements via the signal lines, converts an electric charge to an electric signal for each of the radiation detection elements, and outputs the electric signal as image data;
a thinned-out data preparing section for thinning and, from the image data, abstracting image data per scanning line unit and preparing thinned-out data; and
a compression section which performs compression processing to the thinned-out data,
wherein the compression section performs compression processing to thinned-out data adjoining in a direction of the signal line, or performs compression processing to difference data for the thinned-out data adjoining in the direction of the signal line by calculating difference for the thinned-out data adjoining in the direction of the signal line and generating the difference data.

15. The radiographic-image capturing device described in claim 14,
wherein the thinned-out data preparing section thins and abstracts image data per signal line unit.

16. A radiographic-image capturing system comprising:
the radiographic-image capturing device described in claim 14 provided with a transfer section transferring the predetermined image data subjected to the compression processing or the difference data subjected to the compression processing; and
a console for preparing thinned out image by restoring the original predetermined image data based on the thinned out data subjected to the compression processing transferred from the radiographic-image capturing device, or the difference data subjected to the compression processing transferred from the radiographic-image capturing device.

* * * * *